United States Patent
Boden et al.

(10) Patent No.: US 11,179,501 B2
(45) Date of Patent: *Nov. 23, 2021

(54) BONE MORPHOGENETIC PROTEIN PATHWAY ACTIVATION, COMPOSITIONS FOR OSSIFICATION, AND METHODS RELATED THERETO

(71) Applicant: Emory University, Atlanta, GA (US)

(72) Inventors: Scott D. Boden, Atlanta, GA (US); Sreedhara Sangadala, Dallas, GA (US)

(73) Assignee: Emory University, Atlanta, GA (US)

( * ) Notice: Subject to any disclaimer, the term of this patent is extended or adjusted under 35 U.S.C. 154(b) by 54 days.

This patent is subject to a terminal disclaimer.

(21) Appl. No.: 16/370,003

(22) Filed: Mar. 29, 2019

(65) Prior Publication Data

US 2019/0224378 A1 Jul. 25, 2019

Related U.S. Application Data

(63) Continuation of application No. 15/250,221, filed on Aug. 29, 2016, now Pat. No. 10,286,113, which is a
(Continued)

(51) Int. Cl.

| | | |
|---|---|---|
| *A61L 27/54* | (2006.01) | |
| *A61K 31/05* | (2006.01) | |
| *A61K 31/07* | (2006.01) | |
| *A61K 31/136* | (2006.01) | |
| *A61K 31/196* | (2006.01) | |
| *A61K 31/203* | (2006.01) | |
| *A61K 31/404* | (2006.01) | |
| *A61K 31/407* | (2006.01) | |
| *A61K 31/4174* | (2006.01) | |
| *A61K 31/4184* | (2006.01) | |
| *A61K 31/4745* | (2006.01) | |
| *A61K 31/475* | (2006.01) | |
| *A61K 31/506* | (2006.01) | |
| *A61K 31/5377* | (2006.01) | |
| *A61K 31/585* | (2006.01) | |
| *A61K 31/704* | (2006.01) | |
| *A61K 31/7048* | (2006.01) | |
| *A61K 31/7068* | (2006.01) | |
| *A61K 38/18* | (2006.01) | |
| *A61K 31/232* | (2006.01) | |

(Continued)

(52) U.S. Cl.
CPC .............. *A61L 27/54* (2013.01); *A61K 31/05* (2013.01); *A61K 31/07* (2013.01); *A61K 31/136* (2013.01); *A61K 31/196* (2013.01); *A61K 31/203* (2013.01); *A61K 31/232* (2013.01); *A61K 31/404* (2013.01); *A61K 31/407* (2013.01); *A61K 31/4174* (2013.01); *A61K 31/4184* (2013.01); *A61K 31/436* (2013.01); *A61K 31/475* (2013.01); *A61K 31/4745* (2013.01); *A61K 31/506* (2013.01); *A61K 31/5377* (2013.01); *A61K 31/56* (2013.01); *A61K 31/585* (2013.01); *A61K 31/704* (2013.01); *A61K 31/7048* (2013.01); *A61K 31/7068* (2013.01); *A61K 33/42* (2013.01); *A61K 38/1875* (2013.01); *A61K 38/39* (2013.01); *A61L 27/12* (2013.01); *A61L 27/24* (2013.01); *A61L 27/46* (2013.01); *A61L 27/52* (2013.01); *A61L 2300/414* (2013.01); *A61L 2300/45* (2013.01); *A61L 2430/02* (2013.01)

(58) Field of Classification Search
None
See application file for complete search history.

(56) References Cited

U.S. PATENT DOCUMENTS

| | | |
|---|---|---|
| 5,258,389 A | 11/1993 | Goulet et al. |
| 5,350,748 A | 9/1994 | Boschelli |

(Continued)

FOREIGN PATENT DOCUMENTS

| | | |
|---|---|---|
| WO | 2000047214 | 8/2000 |
| WO | 2002067820 | 9/2002 |

(Continued)

OTHER PUBLICATIONS

Bratton et al., "Discovery of pyrrole-based hepatoselective 1 igands as potent inhibitors of HMG-CoA reductase", Bioorganic &Medicinal Chemistry, 2007, vol. 15, pp. 5576-5589.
(Continued)

*Primary Examiner* — Melissa L Fisher
(74) *Attorney, Agent, or Firm* — Emory Patent Group

(57) ABSTRACT

The disclosure relates to compounds and compositions for bone formation, fracture treatment, bone grafting, bone fusion, cartilage maintenance and repair and methods related thereto. In certain embodiments, the disclosure relates to compositions comprising one or more compound(s) disclosed herein, such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salt thereof, for use in bone growth processes. In a typical embodiment, a bone graft composition is implanted in a subject at a site of desired bone growth or enhancement.

14 Claims, 17 Drawing Sheets

Specification includes a Sequence Listing.

Related U.S. Application Data continuation of application No. 14/345,661, filed as application No. PCT/US2012/055722 on Sep. 17, 2012, now abandoned.

(60) Provisional application No. 61/669,199, filed on Jul. 9, 2012, provisional application No. 61/657,099, filed on Jun. 8, 2012, provisional application No. 61/536,168, filed on Sep. 19, 2011.

(51) Int. Cl.
| | | |
|---|---|---|
| *A61K 31/56* | (2006.01) | |
| *A61K 33/42* | (2006.01) | |
| *A61L 27/12* | (2006.01) | |
| *A61L 27/46* | (2006.01) | |
| *A61L 27/52* | (2006.01) | |
| *A61K 31/436* | (2006.01) | |
| *A61K 38/39* | (2006.01) | |
| *A61L 27/24* | (2006.01) | |

(56) References Cited

U.S. PATENT DOCUMENTS

| | | | |
|---|---|---|---|
| 6,015,815 | A | 1/2000 | Mollison |
| 6,037,519 | A | 3/2000 | McKay |
| 6,833,353 | B1 | 12/2004 | Fujisawa |
| 7,615,562 | B2 | 11/2009 | Bollbuck |
| 10,286,113 | B2 | 5/2019 | Boden |
| 2002/0193883 | A1 | 12/2002 | Wironen |
| 2003/0055511 | A1 | 3/2003 | Schryver |
| 2007/0060590 | A1 | 3/2007 | Shoda |
| 2007/0065484 | A1 | 3/2007 | Chudzik |
| 2007/0077267 | A1 | 4/2007 | Molz |
| 2007/0116689 | A1 | 5/2007 | Boden |
| 2007/0154563 | A1 | 7/2007 | Behnam |
| 2007/0232703 | A1 | 10/2007 | Erina |
| 2009/0029912 | A1 | 1/2009 | Gronthos |
| 2009/0054313 | A9 | 2/2009 | Marx |
| 2009/0061071 | A1 | 3/2009 | McMorrow |
| 2009/0221503 | A1 | 9/2009 | Kneissel |
| 2009/0234100 | A9 | 9/2009 | Boden |
| 2009/0253656 | A1 | 10/2009 | Yamazaki |
| 2010/0032090 | A1 | 2/2010 | Myung |
| 2010/0119538 | A9 | 5/2010 | Boden |
| 2010/0266661 | A1 | 10/2010 | McKay |
| 2012/0316111 | A1 | 12/2012 | Rossini |
| 2013/0137634 | A1 | 5/2013 | Boden |
| 2013/0344165 | A1 | 12/2013 | Boden |

FOREIGN PATENT DOCUMENTS

| | | |
|---|---|---|
| WO | 2005005434 | 1/2005 |
| WO | 2005096990 | 10/2005 |
| WO | 2006029081 | 3/2006 |
| WO | 2009017269 | 2/2009 |
| WO | 2012116135 | 8/2012 |
| WO | 2013043529 | 3/2013 |
| WO | 2014011540 | 1/2014 |

OTHER PUBLICATIONS

Ester et al., "Novel Derivatives of Pyridylbenzo[blthiophene-2-carboxamides and Benzo[b]thieno[2,3-c]naphthyridin-2-ones: Minor Structural Variations Provoke Major Differences of Anti tumor Action Mechanisms", Journal of Medicinal Chemistry, 2009, vol. 52, No. 8, pp. 2482-2492.

FDA Label 2008 Prograf®, tacrolimus capsules, tacrolimus injection (for intravenous infusion only).

Gazit et al., Tyrphostins 2 Heterocyclic and a-Substituted Benzylidenemalononitrile Tyrphostins as Potent Inhibitors of EGF Receptor and ErbB2/neu Tyrosine Kinases J. Med. Chem. 1991, 34, 1896-1907.

Groppe et al., Structural basis of BMP signalling inhibition by the cystine knot protein Noggin, Nature, 2002, 420, 636-642.

Kaihara et al. Effect of FK506 on osteoinduction by recombinant human bone morphogenetic protein-2Life Sciences 72 (2002) 247-256.

Kalantar-Zadeh et al. Management of Minerals and Bone Disorders after Kidney Transplantation, Curr Opin Nephrol Hypertens, 2012, 21(4): 389-403.

Lee et al. Rapamycin promotes the osteoblastic differentiation of human embryonic stem cells by blocking the mTOR pathway and stimulating the BMP/Smad pathway. Stem Cells Dev. 2010;19:557-68.

| BMPR-1A (1rew) | BMPR-II (2hlr) | BMP-2 (1rew) | |
|---|---|---|---|
| Gly-42 | Tyr-40 | Asp-25 | Leu-66 |
| His-43 | Leu-69 | Gly-27 | Ser-69 |
| Pro-45 | Lys-81 | Trp-28 | Val-70 |
| Asp-67 | Cys-84 | Trp-31 | Ser-72 |
| Cys-77 | Trp-85 | Val-33 | Lys-76 |
| Lys-79 | Ser-86 | Ala-34 | Ser-85 |
| Glu-81 | His-87 | Pro-35 | Ala-86 |
| Gly-82 | Ile-88 | His-39 | Ile-87 |
| Asp-84 | Gly-89 | Phe-49 | Ser-88 |
| Phe-85 | Asp-90 | Pro-50 | Leu-90 |
| Gln-86 | Glu-93 | Ala-52 | Glu-96 |
| Lys-88 | Tyr-113 | Asp-53 | Lys-97 |
| Asp-89 | Phe-115 | His-54 | Val-98 |
| Ser-90 | | Ser-57 | Lys-100 |
| Lys-92 | | Asn-59 | Lys-101 |
| Gln-94 | | Ile-62 | Asp-102 |
| Arg-97 | | | Tyr-103 |

BONE MORPHOGENETIC PROTEIN PATHWAY ACTIVATION, COMPOSITIONS FOR OSSIFICATION, AND METHODS RELATED THERETO

CROSS REFERENCE TO RELATED APPLICATIONS

This application is a continuation of U.S. application Ser. No. 15/250,221 filed Aug. 29, 2016, which is a continuation of U.S. application Ser. No. 14/345,661 filed Mar. 19, 2014, which is the National Stage Application of PCT/US2012/055722 filed Sep. 17, 2012, which claims priority to U.S. Provisional Application No. 61/536,168 filed Sep. 19, 2011, U.S. Provisional Application No. 61/657,099 filed Jun. 8, 2012, and U.S. Provisional Application No. 61/669,199 filed Jul. 9, 2012. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 11221USCON2_ST25.txt. The text file is 9 KB, was created on Mar. 29, 2019, and is being submitted electronically via EFS-Web.

FIELD

This disclosure relates to compounds and compositions for bone formation, fracture treatment, bone grafting, bone fusion, cartilage maintenance and repair, and methods related thereto. In certain embodiments, the disclosure relates to bone graft compositions comprising one or more compound(s) disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof. In a typical embodiment, a bone graft composition is implanted in a subject at a site of desired bone growth or enhancement.

BACKGROUND

Bone grafting is typically performed for spinal fusions, after cancerous bone removal, and in certain operations, e.g., plastic surgery. The iliac crest is often used as a donor site for autologous grafts. Complications collecting bone from the iliac crest include pain, nerve damage, hematoma and wound complications, avulsion of the anterior superior iliac spine (ASIS), hematoma, herniation of the abdominal cavity contents, and cosmetic deformity. Thus, it is desirable to develop materials and methods of forming bone that do not require harvesting bone from remote sites of the patient.

Synthetic bone grafts typically include a matrix that holds minerals and other salts. Natural bone has an intracellular matrix mainly composed of type I collagen, and some synthetic bone grafts include a collagen matrix. Synthetic bone grafts typically contain bone growth factors such as bone morphogenetic proteins (BMPs) because of their ability to induce ossification in the matrix material. Recombinant human BMP-2 has been approved by the FDA in synthetic bone grafts such as INFUSE™. INFUSE™ is approved for open tibial shaft fractures, lumbar interbody fusion, and sinus and alveolar ridge augmentations. However, the high cost and need for high concentrations of BMP-2 for treatment creates a barrier for routine clinical use. Thus, there is a need to identify additional compositions that can substitute or complement the use of BMPs in treating bone-related conditions.

Conflicting reports provide that sirolimus and everolimus have a bearing on osteoblast proliferation and differentiation or decreasing osteoclast-mediated bone resorption. See Kalantar-Zedah et al., Curr Opin Nephrol Hypertens., 2012, 21(4):389-403, Lee et al., Stem Cells Dev., 2010, 19(4):557-68, WO2009017269, WO2005/005434 (U.S. application Ser. No. 12/398,225), U.S. Pat. Nos. 5,258,389 and 6,015,815. References cited herein are not an admission of prior art.

SUMMARY

This disclosure relates to compounds and compositions for ossification and methods related thereto. In certain embodiments, it is an object of the disclosure to provide certain compounds, compositions, and methods of using these compounds to improve bone formation, fracture treatment, bone grafting, bone fusion, cartilage maintenance and repair in a subject. In a typical embodiment, the bone graft composition comprises a compound disclosed herein or derivatives that modulates BMP and/or BMPR interactions with their natural target proteins. In specific embodiments, the disclosure relates to compounds, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14,15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan, 9-aminocamptothecin; sunitinib or derivatives; and compositions including such compounds, as well as their methods of use.

Examples of additional contemplated compounds include 1-[(2-chlorophenyl) diphenylmethyl]-1H-imidazole, derivatives, or salts thereof, such as clotrimazole; 3',5-di-2-propen- 1-yl-[1,1'-biphenyl]-2,4'-diol, derivatives, or salts thereof such as honokiol; 5,6,8,11,12,13,14,15, 16,17,18,19,24,25, 26,26a-hexadecahydro-5,19-dihydroxy-3-[(1E)-2-[4-hydroxy-3-methoxycyclohexyl]-1-methylethenyl]-14,16-dimethoxy-4,10,12,18-tetramethyl-8-(2-propen-1-yl)-15,19-epoxy-3H-pyrido[2,1-c][1,4]oxaazacyclotricosine-1,7,20, 21(4H,23H)-tetrone, derivatives, or salts thereof such as tacrolimus; 6,9-difluoro-11-hydroxy-16-methyl-3-oxo-17-(1-oxopropoxy)-androsta-1,4-diene-17-carbothioic acid S-(fluoromethyl) ester, derivatives, or salts thereof such as fluticasone propionate, derivatives, or salts thereof; N-[[(5S)-3-[3-fluoro-4-(4-morpholinyl)phenyl]-2-oxo-5-oxazolidinyl]methyl]-acetamide, derivatives, or salts thereof such as linezolid; and, 4'-((1,7'-dimethyl-2'-propyl-1H,3'H-[2,5'-bibenzo[d]imidazol]-3'-yl)methyl)[1,1'-biphenyl]-2-carboxylic acid, derivatives, or salts thereof such as telmisartan; and 9,10,12,13,14,21,22,23,24,25,26,27,32,33,34, 34a-Hexadecahydro-9,27-dihydroxy-3-[2-[4-hydroxy-3-methoxycyclohexyl]-1-methylethyl]-10,21-dimethoxy-6,8, 12,14,20,26-hexamethyl-23,27-epoxy-3H-pyrido[2,1-c][1, 4]oxaazacyclohentriacontine-1,5,11,28,29(4H,6H,31H)-pentone, derivatives, or salts thereof such as sirolimus, everolimus, and temsirolimus.

Other contemplated compounds include those from the following list: capsaicin—chemical name N-(4-hydroxy-3-methoxybenzyl)-8-methylnon-6-enamide; dihydrocapsaicin; nordihydrocapsaicin; homodihydrocapsaicin; homocapsaicin; nonivamide; diphenylcyclopropenone—chemical name 2,3-diphenylcycloprop-2-enone; estradiol—chemical name (8R,9S,13S,14S,17S)-13-methyl-7,8,9,11,12,13,14, 15,16,17-decahydro-6H-cyclopenta[a]phenanthrene-3,17-diol; ketoconazole—chemical name 1-(4-(4-(((2R,4S)-2-((1H-imidazol-1-yl)methyl)-2-(2,4-dichlorophenyl)-1,3-dioxolan-4-yl)methoxy)phenyl)piperazin-1-yl)ethanone; ethynylestradiol—chemical name (8R,9S,13S,14S,17R)-17-ethynyl-13-methyl-7,8,9,11,12,13,14,15,16,17-decahydro-6H-cyclopenta[a]phenanthrene-3,17-diol; progesterone—chemical name (8S,9S,10R,13S,14S,17S)-17-acetyl-10,13-dimethyl-6,7,8,9,10,11,12,13,14,15,16,17-dodecahydro-1H-cyclopenta[a]phenanthren-3(2H)-one; salbutamol—chemical name 4-(2-(tert-butylamino)-1-hydroxyethyl)-2-(hydroxymethyl)phenol; zardaverine—chemical name 6-(4-(difluoromethoxy)-3-methoxyphenyl)pyridazin-3-ol; riluzole—chemical name 6-(trifluoromethoxy)benzo[d]thiazol-2-amine; 9-chloro-2-(furan-2-yl)-[1,2,4]triazolo[1,5-c] quinazolin-5-amine; prazosin—chemical name (4-(4-amino-6,7-dimethoxyquinazolin-2-yl)piperazin-1-yl)(furan-2-yl)methanone hydrochloride hydrate; urapidil—chemical name 6-((3-(4-(2-methoxyphenyl)piperazin-1-yl)propyl) amino)-1,3-dimethylpyrimidine-2,4(1H,3H)-dione hydrochloride; naftopidil; carmofur—chemical name 5-fluoro-N-hexyl-2,4-dioxo-3,4-dihydropyrimidine-1(2H)-carboxamide; 5-fluoro-N-alkyl-2,4-dioxo-3,4-dihydropyrimidine-1(2H)-carboxamide; fluorouracil; itraconazole—chemical name 4-(4-(4-(4-((2((1H-1,2,4-triazol-1-yl)methyl)-2-(2,4-dichlorophenyl)-1,3-dioxolan-4-yl)methoxy)phenyl)piperazin-1-yl)phenyl)-1-(sec-butyl)-1H-1,2,4-triazol-5(4H)-one; posaconazole; trimebutine—chemical name 2-(dimethylamino)-2-phenylbutyl 3,4,5-trimethoxybenzoate; piceid—chemical name (2S,3R,4S,5S, 6R)-2-(3-hydroxy-5-((E)-4-hydroxystyryl)phenoxy)-6-(hydroxymethyl)tetrahydro-2H-pyran-3,4,5-triol; resveratrol; megestrol acetate—chemical name (8R,9S,10R, 13S,14S,17R)-17-acetyl-6,10,13-trimethyl-3-oxo-2,3,8,9, 10,11,12,13,14,15,16,17-dodecahydro-1H-cyclopenta[a] phenanthren-17-yl acetate; docetaxel—chemical name (2aR,4S,4aS,6R,9S,11R,12S,12aR,12b S)-12b-acetoxy-9-(((2R,3S)-3-((tert-butoxycarbonyl)amino)-2-hydroxy-3-phenylpropanoyl)oxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b] oxet-12-yl benzoate; paclitaxel; perospirone—chemical name (3aR,7aS)-2-(4-(4-(benzo[d]isothiazol-3-yl)piperazin-1-yl)butyl)hexahydro-1H-isoindole-1,3(2H)-dione hydrochloride; alprazolam—chemical name 8-chloro-1-methyl-6-phenyl-4H-benzo[f][1,2,4]triazolo[4,3-a][1,4]diazepine; diazepam; oxazepam; temazepam; lorazepam; clonazepam; midazolam; fenoldopam—chemical name 6-chloro-1-(4-hydroxyphenyl)-2,3,4,5-tetrahydro-1H-benzo[d]azepine-7,8-diol methanesulfonate; ondansetron—chemical name 9-methyl-3-((2-methyl-1H-imidazol-1-yl)methyl)-2,3-dihydro-1H-carbazol-4(9H)-one; letrozole—chemical name 4,4'-((1H-1,2,4-triazol-1-yl)methylene)dibenzonitrile; taxifolin—chemical name (2R,3S)-2-(3,4-dihydroxyphenyl)-3, 5,7-trihydroxychroman-4-one; cytarabine; methyltestosterone—chemical name (8R,9S,10R,13S,14S,17S)-17-hydroxy-10,13,17-trimethyl-6,7,8,9,10,11,12,13,14,15,16, 17-dodecahydro-1H-cyclopenta[a]phenanthren-3(2H)-one; artesunate—chemical name 4-oxo-4-(((3R,5aS,6R,8aS,9R, 10R,12R,12aR)-3,6,9-trimethyldecahydro-3H-3,12-epoxy [1,2]dioxepino[4,3-i]isochromen-10-yl)oxy)butanoic acid; artemether; dihydroartemisinin; artelinic acid; artenimol; artemotil; triclabendaxole—chemical name 5-chloro-6-(2,3-dichlorophenoxy)-2-(methylthio)-1H-benzo[d]imidazole; albendazole; mebendazole; thiabendazole; fenbendazole; flubendazole; ezetimibe—chemical name (3R,4S)-1-(4-fluorophenyl)-3-((S)-3-(4-fluorophenyl)-3-hydroxypropyl)-4-(4-hydroxyphenyl)azetidin-2-one; oxiconazole—chemical name 1-(2,4-dichlorophenyl)-2-(1H-imidazol-1-yl) ethanone O-(2,4-dichlorobenzyl) oxime; gebexate—chemical name ethyl 4-((6-((diaminomethylene)amino) hexanoyl)oxy)benzoate; risperidone—chemical name 3-(2-(4-(6-fluorobenzo[d]isoxazol-3-yl)piperidin-1-yl)ethyl)-2-methyl-6,7,8,9-tetrahydro-4H-pyrido[1,2-a]pyrimidin-4-one; paliperidone; bifonazole—chemical name 1-([1,1'-biphenyl]-4-yl(phenyl)methyl)-1H-imidazole; indinavir; calcitriol; vinorelbine; tegaserod; irbesartan; pterostilbene; lovastatin; felodipine; daunorubicin hydrochloride; albendazole; mitoxantrone; clomid; econazole nitrate; 5-fluorouracil; including derivatives and those substituted with one or more substituents, which are the same or different, or salts thereof.

In certain embodiments, bone graft compositions comprise compounds disclosed herein and a bone morphogenetic protein and/or another growth factor. Typically, the bone morphogenetic protein is BMP-2, BMP-5, or BMP-7. In certain embodiments, the graft composition comprises calcium phosphates and/or bone granules, hydroxyapatite and/or beta-tricalcium phosphate, alpha-tricalcium phosphate, polysaccharides or combinations thereof. Crushed bone granules, typically obtained from the subject, are optionally added to the graft composition.

In some embodiments, the graft contains osteogenic material can be obtained from autogenic or allogenic sources and includes, autograft, autogenic bone marrow aspirate, autogenic lipoaspirate, allogenic bone marrow aspirate, allogenic lipoaspirate, and blends and mixtures thereof.

In some embodiments, the disclosure relates to bone graft compositions comprising a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14, 15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl) butanoic acid derivatives, or salts thereof such as chlorambucil, podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof and a graft matrix. Typically, the matrix comprises a collagen sponge and/or a compression resistant type I collagen and calcium phosphates. In other embodiments, the matrix is a hydrogel.

In certain embodiments, the disclosure contemplates a graft composition or matrix comprising compounds disclosed herein such as tacrolimus, pimecrolimus, sirolimus, everolimus, temsirolimus, teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, wherein the graft matrix is a collagen or demineralized bone matrix or ceramic of other scaffold disclosed herein without exogenous cells.

In some embodiments, the disclosure relates to kits comprising a graft composition, a compound disclosed herein, and a graft matrix. In certain embodiments, the kits further comprise a bone morphogenetic protein and/or another growth factor. In certain embodiments, the kits further comprise a transfer device, such as a syringe or pipette.

In some embodiments, the disclosure relates to methods of generating BMP-mediated osteoblasts comprising administering an effective amount of compound(s) disclosed herein to cells capable of osteoblastic differentiation, such as mesenchymal stem cells and pre-osteoblastic cells.

In some embodiments, the disclosure relates to methods of forming bone or cartilage, comprising implanting a graft composition comprising a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14,15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil, podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof in a subject under conditions such that bone or cartilage forms in the graft. Typically, the subject has a void in the bony structure wherein the graft composition is implanted in the void. In certain embodiments, the void is in a bone selected from an extremity, maxilla, mandible, pelvis, spine and/or cranium. In certain embodiments, the void is a result of surgical removal of bone. In certain embodiments, the void is between bone and an implanted medical device. In another embodiment, the method further comprises the step of securing movement of bone structure with a fixation system, and removing the system after bone forms in the implanted graft.

In certain embodiments, the disclosure contemplates local bone formation for fracture repair, segmental bone defects, spine fusion, bone grafting, and regional bone enhancement for osteopenic bones before they fracture (e.g. hip, vertebral body, etc) by deliver locally to induce local bone formation.

In certain embodiments, the disclosure relates to methods of growing bone in subject by locally administering, such as by injection, a composition comprising a compound disclosed herein, optionally in combination with a growth factor, about the area of desired bone growth. In certain embodiments, the disclosure relates to methods of growing bone comprising administering a pharmaceutical composition comprising clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or pharmaceutically acceptable salts thereof to a subject in an area of desired growth, wherein the administration is localized directly about the area of desired growth. In certain embodiments, the administration is not oral administration. In certain embodiments, the administration is through a catheter or hypodermic needle with a tip that is not in a vein. In certain embodiments, the administration is by injection into the subcutaneous tissue or in or about an area typically occupied by bone or between vertebra, e.g., in the area usually occupied by in the intervertebral disc, to form a spinal fusion.

In certain embodiments, the method contemplates implanting a graft composition in a desired area of the subject and locally administering a composition comprising a compound disclosed herein, optionally in combination with a growth factor, in the graft or about the area of the graft implant such as by injection.

In certain embodiments, the disclosure relates to uses of compounds disclosed herein for cartilage regeneration e.g., between intervertebral disc and articular, jaw, elbow, knee, ankle, wrist, and hip joints. Methods contemplate oral administration, intravenous administration, or direct injection at the desired site(s) of the subject.

In some embodiments, the disclosure relates to methods of performing spinal fusion comprising implanting a bone graft composition comprising a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14,15,16,17-dodecahydro-3H-cyclopenta [a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil, podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof configured to grow bone between two vertebrae of a subject. In certain embodiments, the composition further comprises a bone morphogenetic protein and/or another growth factor. In a typical embodiment, the subject is diagnosed with degenerative disc disease or has symptoms of back pain.

In some embodiments, the disclosure relates to methods of inserting a prosthetic device or anchor, comprising exposing a bone and implanting a graft composition comprising a compound disclosed herein in contact with the bone. In certain embodiments, one implants the prosthetic device or anchor in the graft composition. In certain embodiments, the composition further comprises a bone morphogenetic protein and/or another growth factor.

In some embodiments, the disclosure relates to pharmaceutical compositions comprising compounds disclosed herein or pharmaceutically acceptable salts thereof. In certain embodiments, the composition further comprises a bone morphogenetic protein and/or another growth factor. In certain embodiments, the pharmaceutical composition is formulated to release over a 12 hour, 1 day, 3 day, 5 day, 7 day, two week, or one month period.

In certain embodiments, the disclosure relates to methods of preventing or treating a bone fracture, comprising administering a pharmaceutical composition comprising a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14, 15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl) oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(diethylamino)phenyl)butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof or a pharmaceutically acceptable salt thereof, to a subject at risk for, exhibiting symptoms of, or diagnosed with a bone fracture. In certain embodiments, the composition further comprises a bone morphogenetic protein and/or another growth factor.

In certain embodiments, the administration is localized. In certain embodiments, administration is achieved through oral delivery, intravenous delivery, parenteral delivery, intradermal delivery, percutaneous delivery, or subcutaneous delivery. In some embodiments, the method further comprises the step of exposing the bone fracture to pulsed electromagnetic fields. In further embodiments, the subject is diagnosed with a long bone shaft fracture such as a tibia or femur fracture corrected with intramedullary nail fixation.

In some embodiments, the disclosure relates to methods of preventing or treating a bone degenerative disease, comprising administering a pharmaceutical composition comprising a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13, 14, 15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl) oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(diethylamino)phenyl) butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof or a pharmaceutically acceptable salts thereof, to a subject at risk for, exhibiting symptoms of, or diagnosed with a bone degenerative disease. In certain embodiments, the composition further comprises a bone morphogenetic protein and/or another growth factor. In certain embodiments, the administration is systemic, or administration is achieved through oral delivery, intravenous delivery, parenteral delivery, intradermal delivery, percutaneous delivery, or subcutaneous delivery. In some embodiments, the disease is osteoporosis, osteitis deformans, bone metastasis, multiple myeloma, primary hyperparathyroidism, or osteogenesis imperfecta.

In some embodiments, the disclosure relates to methods for decreasing the time required to form new bone in the presence of a bone morphogenetic protein, comprising co-administering at least one compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14, 15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof and another active ingredient.

In some embodiments, the disclosure relates to a process for engineering bone tissue comprising combining a compound disclosed herein, such as 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14, 15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin;

anthraquinone derivatives such as mitoxantrone and pixantrone; plicamycin or derivatives; pazopanib or derivatives; camptothecin or derivatives such as topotecan, irinotecan; sunitinib or derivatives or salts thereof and optionally a bone morphogenetic protein, with a cell selected from the group consisting of osteogenic cells, pluripotent stem cells, mesenchymal cells, and embryonic stem cells.

In certain embodiments, the disclosure relates to using 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8, 9,10,11,12,13,14, 15,16,17-dodecahydro-3H-cyclopenta[a] phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(dialkylamino)phenyl)butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof in the production of a medicament for the treatment or prevention of a bone disease or other applications disclosed herein.

In certain embodiments, the disclosure relates to a bone graft composition comprising a bone growth-inducing amount of 1-triarylmethyl-1H-imidazole derivatives, or salts thereof, such as clotrimazole; biphenyl-diol derivatives, or salts thereof such as honokiol and magnolol; macrolide lactone derivatives, or salts thereof such as tacrolimus, pimecrolimus, sirolimus, everolimus, temsirolimus; steroid derivatives, or salts thereof such as spironolactone; 3-oxo-6,7,8,9,10,11,12,13,14,15,16,17-dodecahydro-3H-cyclopenta[a]phenanthrene-17-carbothioic acid derivatives, or salts thereof such as fluticasone, fluticasone propionate, and fluticasone furoate; 3-(4-morpholinophenyl)oxazolidin-2-one derivatives, or salts thereof such as linezolid; 1H,3'H-2,5'-bibenzo[d]imidazole derivatives or salts thereof such as telmisartan; rentinol derivatives, or salts thereof such as tretinoin, alitretinoin, isotretinoin, retinol, etretinate, acitretin; 4-(4-(diethylamino)phenyl) butanoic acid derivatives, or salts thereof such as chlorambucil; podophyllotoxin derivatives such as teniposide; aziridine derivatives such as mitomycin C; nucleoside derivatives such as cytarabine, decitabine; vinca alkaloid derivatives such as vinorelbine, vinblastine, vincristine, and vindesine; anthracycline doxorubicin derivatives such as doxorubicin, valrubicin, daunorubicin, epirubicin, idarubicin; anthraquinone derivatives such as mitoxantrone and pixantrone; plicamycin or derivatives; pazopanib or derivatives; camptothecin or derivatives such as topotecan, irinotecan; sunitinib or derivatives or salts thereof and a pharmaceutically acceptable carrier.

In certain embodiments, the derivative is 1-triarylmethyl-1H-imidazole or salt thereof with one or more substituents.

In certain embodiments, the derivative is 1,1'-biphenyl-2,4'-diol or salt thereof with one or more substituents.

In certain embodiments, the derivative is 5,6,8,11,12,13, 14,15,16,17,18,19,24,25,26,26a-hexadecahydro-3-[(1E)-2-[cyclohexyl]ethenyl]-15,19-epoxy-3H-pyrido[2,1-c][1,4] oxaazacyclotricosine-1,7,20,21(4H,23H)-tetrone or salt thereof with one or more substituents.

In certain embodiments, the derivative is 3-oxo-6,7,8,9, 10,11,12,13,14,15,16,17-dodecahydro-3H-cyclopenta[a] phenanthrene-17-carbothioic acid or salt thereof with one or more substituents.

In certain embodiments, the derivative is 1,6,7,8,9,10,11, 12,13,14,15,16-dodecahydro-3'H-spiro[cyclopenta[a] phenanthrene-17,2'-furan]-3,5'(2H,4'H)-dione or salt thereof with one or more substituents.

In certain embodiments, the derivative is 3-(4-morpholinophenyl)oxazolidin-2-one or salt thereof with one or more substituents.

In certain embodiments, the derivative is 1-(octa-1,3,5,7-tetraen-1-yl)cyclohex-1-ene or octa-1,3,5,7-tetraen-1-ylbenzene or salt thereof with one or more substituents.

In certain embodiments, the derivative is 3'-([1,1'-biphenyl]-4-ylmethyl)-1H,3'H-2,5'-bibenzo[d]imidazole or salt thereof with one or more substituents.

In certain embodiments, the derivative is 4-(4-(dialkylamino)phenyl)butanoic acid or salt thereof with one or more substituents.

In certain embodiments, the 1-triarylmethyl-1H-imidazole derivative is clotrimazole or salt thereof optionally substituted with one or more substituents.

In certain embodiments, the biphenyl-diol derivative is honokiol or magnolol or salt thereof optionally substituted with one or more substituents.

In certain embodiments, the macrolide lactone derivative is tacrolimus, pimecrolimus, sirolimus, everolimus, temsirolimus or salt thereof optionally substituted with one or more substituents.

In certain embodiments, the 3-oxo-6,7,8,9,10,11,12,13,14,15,16,17-dodecahydro-3H-cyclopenta[a]phenanthrene-17-carbothioic acid derivative is fluticasone, fluticasone propionate, or fluticasone furoate or salt thereof optionally substituted with one or more substituents.

In certain embodiments, the 3-(4-morpholinophenyl)oxazolidin-2-one derivative is linezolid or salt thereof optionally substituted with one or more substituents.

In certain embodiments, the 1H,3'H-2,5'-bibenzo[d]imidazole derivative is telmisartan or salt thereof optionally substituted with one or more substituents.

In certain embodiments, the steroid derivative is spironolactone or salt thereof optionally substituted with one or more substituents.

In certain embodiments, the retinol derivative is tretinoin, alitretinoin, isotretinoin, retinol, etretinate, acitretin or salt thereof optionally substituted with one or more substituents.

In certain embodiments, the 4-(4-(dialkylamino)phenyl) butanoic acid derivative is chlorambucil or salt thereof with one or more substituents.

In certain embodiments, the podophyllotoxin is 5-phenyl-9-((2-(thiophen-2-yl)hexahydropyrano[3,2-d][1,3]dioxin-6-yl)oxy)-5,5a,8a,9-tetrahydrofuro[3',4':6,7]naphtho[2,3-d][1,3]dioxol-6(8H)-one or derivative such as teniposide optionally substituted with one or more substituents.

In certain embodiments, the aziridine is 1,1a,2,8,8a,8b-hexahydroazirino[2',3':3,4]pyrrolo[1,2-a]indole-4,7-dione or derivative such as mitomycin C optionally substituted with one or more substituents.

In certain embodiments, the nucleoside is 1-(5-methyltetrahydrofuran-2-yl)pyrimidin-2(1H)-one or derivative such as cytarabine, decitabine optionally substituted with one or more substituents.

In certain embodiments, the vinca alkaloid is 9-(2,4,5,6,7,8,9,10-octahydro-1H-3,7-methano[1]azacycloundecino[5,4-b]indol-9-yl)-3a,3a1,4,5,5a,6,11,12-octahydro-1H-indolizino[8,1-cd]carbazole or derivative such as vinorelbine, vinblastine, vincristine, and vindesine optionally substituted with one or more substituents.

In certain embodiments, the anthracycline is 8-acetyl-10-((4-amino-5-hydroxy-6-methyltetrahydro-2H-pyran-2-yl)oxy)-6,8,11-trihydroxy-1-methoxy-7,8,9,10-tetrahydrotetracene-5,12-dione or derivative such as doxorubicin, valrubicin, daunorubicin, epirubicin, idarubicin optionally substituted with one or more substituents.

In certain embodiments, the anthraquinone is anthracene-9,10-dione or derivative such as mitoxantrone and pixantrone optionally substituted with one or more substituents.

In certain embodiments, plicamycin or derivatives are optionally substituted with one or more substituents.

In certain embodiment, pazopanib or derivatives are optionally substituted with one or more substituents.

In certain embodiments, the camptothecin is 1H-pyrano[3',4':6,7]indolizino[1,2-b]quinoline-3,14(4H,12H)-dione or derivatives such as topotecan and irinotecan optionally substituted with one or more substituents.

In certain embodiments, sunitinib or derivatives are optionally substituted with one or more substituents.

In certain embodiments, the bone morphogenetic protein is selected from the group consisting BMP-2, BMP-5, BMP-6, BMP-7, BMP-9, and combinations thereof.

In certain embodiments, the compounds described herein may be used locally such as injection percutaneously at any bone formation site (fracture, spine fusion delayed a day or several days after surgery). In certain embodiments, the compounds may also be bound to a matrix or scaffold and delivered with growth factors, cells (MSCs or others), or on a dry carrier matrix to direct local bone formation in the shape of the carrier/scaffold. Within certain embodiments, it is also contemplated that one or more of these compounds disclosed herein may be used alone or in combination with multiple compounds, with or without exogenous growth factors, and/or in combination with other promoting agents of the BMP pathway such as a noggin inhibitor, a Smurf inhibitor and/or a JAB1 inhibitor.

In certain embodiments, the disclosure contemplates delivery of compositions comprising compounds disclosed herein via a liquid or flowable gel optionally including collagen, hydroxyapatite, demineralized bone, or polymer matrix or others, e.g., as disclosed herein. In certain embodiments, the compositions are injected into the central cavity or interstices of a structural element such as a bone cage made from allograft, polymer thermoplastic, metal such as titanium or aluminum, polyether ether ketone (PEEK) such as those generated from 4,4'-difluorobenzophenone, or other polymer.

In certain embodiments, the disclosure contemplates bone grafts containing more than 10, 15, 20, 25, 30, 35 mM of a compound disclosed herein such as a macrolide lactone derivative such as tacrolimus, pimecrolimus, sirolimus, everolimus, temsirolimus per about 100 mm$^3$, or about 150 mm$^3$, or 50 to 200 mm$^3$, or about 100 to 200 mm$^3$ of bone graft volume. In some embodiments, the disclosure contemplates more than 10 mM or 20 mM of sirolimus. In some embodiments, the disclosure contemplates more than 10 mM or 15 mM of everolimus. In some embodiments, the disclosure contemplates more than 10 mM or 15 mM of tacrolimus. In certain embodiments, the bone graft is contemplated for all uses disclose herein. In certain embodiments, the subject is human.

In certain embodiments, the disclosure contemplates bone graft containing more than 0.7, 0.8, 0.9, 1.0, 1.2, 1.5, 1.8, 2.0, or 3.0 mg of a macrolide lactone derivative such as tacrolimus, pimecrolimus, sirolimus, everolimus, temsirolimus, per about 100 mm$^3$, or about 150 mm$^3$, or 50 to 200 mm$^3$, or about 100 to 200 mm$^3$ of bone graft volume. In some embodiments, the disclosure contemplates more than 1.5 mg of sirolimus. In some embodiments, the disclosure contemplates more that 0.9 mg of everolimus. In some embodiments, the disclosure contemplates more that 0.7 mg of tacrolimus. In certain embodiments, the bone graft is contemplated for all uses disclose herein. In certain embodiments, the subject is human.

In certain embodiments, the disclosure contemplates kit containing a bone graft and a composition comprising more than 0.7, 0.8, 0.9, 1.0, 1.2, 1.5, 1.8, 2.0, or 3.0 mg of a macrolide lactone derivative such as tacrolimus, pimecrolimus, sirolimus, everolimus, temsirolimus per about 100, 125, or 150 mm$^3$ of bone graft volume. In some embodiments, the disclosure contemplates more than 1.5 mg of sirolimus. In some embodiments, the disclosure contemplates more that 0.9 mg of everolimus. In some embodiments, the disclosure contemplates more that 0.7 mg of tacrolimus.

DETAILED DISCUSSION

Terms

Figure 1:
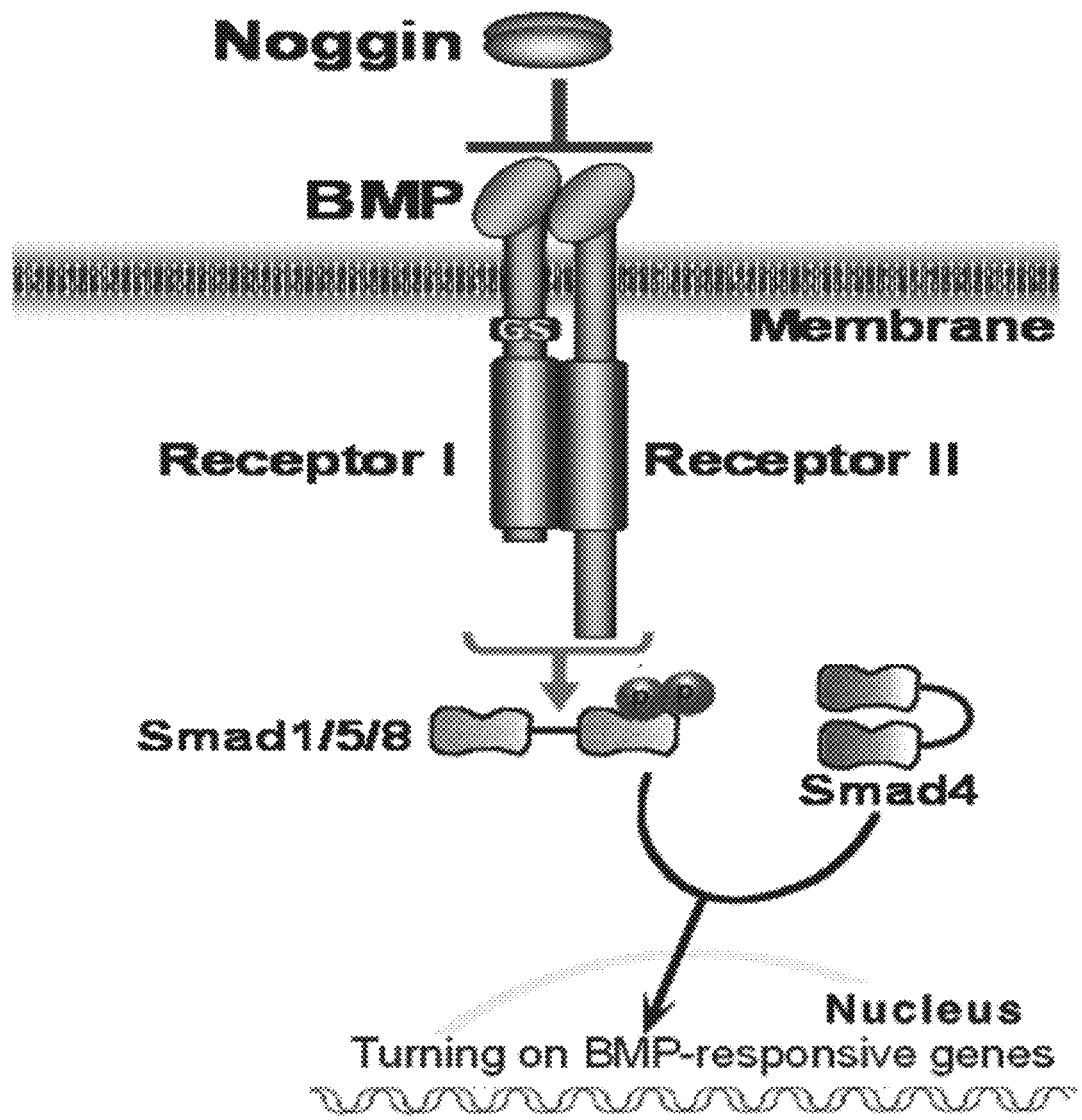
FIG. 1 illustrates the BMP signaling pathway. Although it is not intended that embodiments of the disclosure be limited by any particular mechanism, it is believed that the embodiments may act through the BMP pathway. In the BMP pathway, BMP binds to the BMP receptor type II that in turn activates BMPR-1. Activated BMPR-1 phosphorylates receptor regulated Smads (Smad1/5/8) which form complexes with Smad4 facilitating nuclear entry of Smad complexes. Activated Smad complexes regulate gene expression of BMP-responsive genes. Extracellularly, Noggin antagonizes signaling by binding to BMP and thus inhibiting binding of BMP to its receptor complex.
Figure 2:
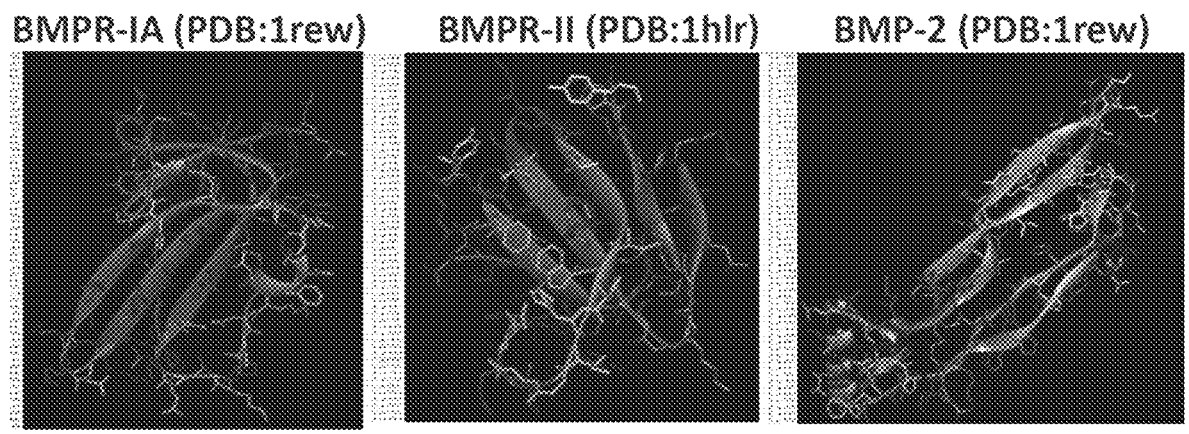
FIG. 2 illustrates the structural features of BMP-Receptor interactions and important amino acids that determine binding specificity and affinity. Illustrative structures of BMP-2, BMPR-IA, and BMPR-II are depicted. Important aminoacids are labeled in 'yellow' color.
Figure 3:
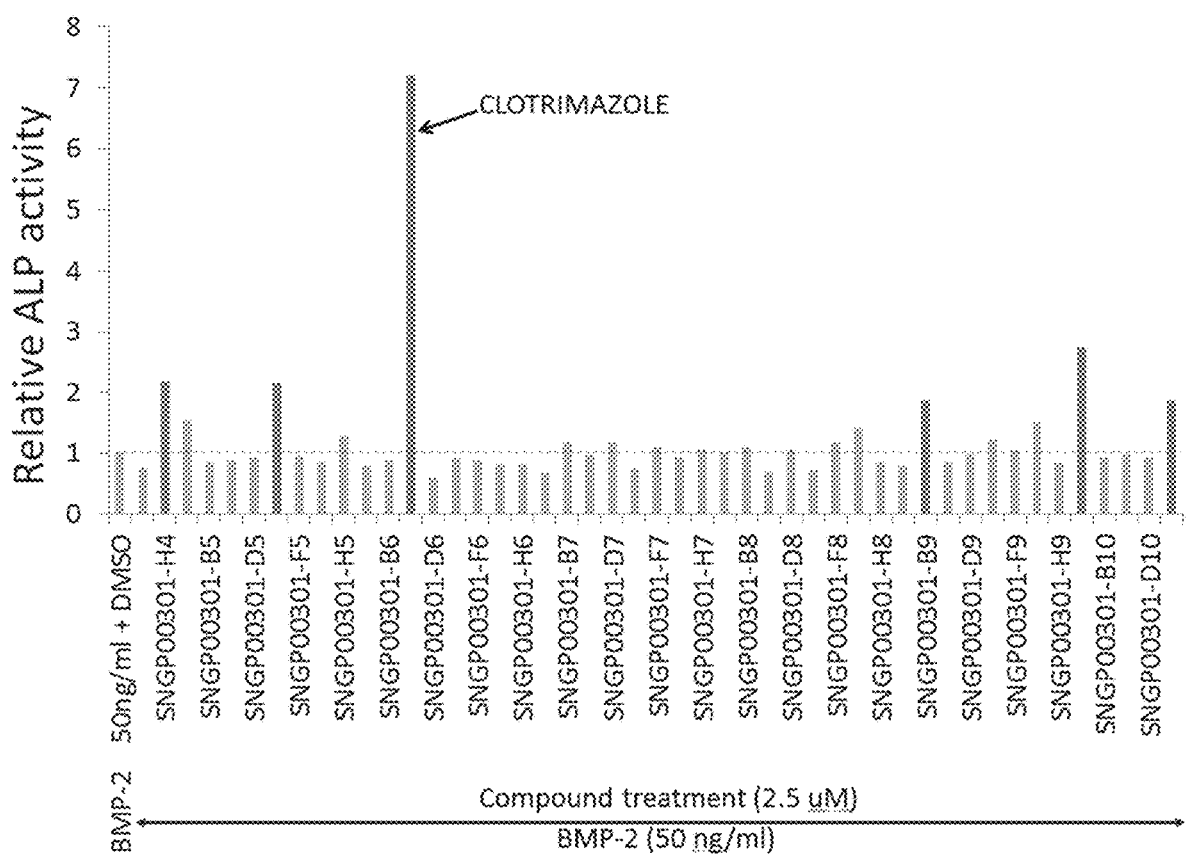
FIG. 3 shows data for the activity of test compounds in the ALP assay. Capsaicin is SNGP-003-01 H04; diphenylcyclopropenone is SNGP-003-01 E05; clotrimazole is SNGP-003-01 C06; beta-estradiol is SNGP-003-01 B09; ketoconazole or 1-(4-(4-(((2R,4S)-2((1H-imidazol-1-yl)methyl)-2-(2,4-dichlorophenyl)-1,3-dioxolan-4-yl)methoxy)phenyl) piperazin-1-yl)ethanone is SNGP-003-01 A10; and ethynylestradiol is SNGP-003-01 E10.
Figure 4:
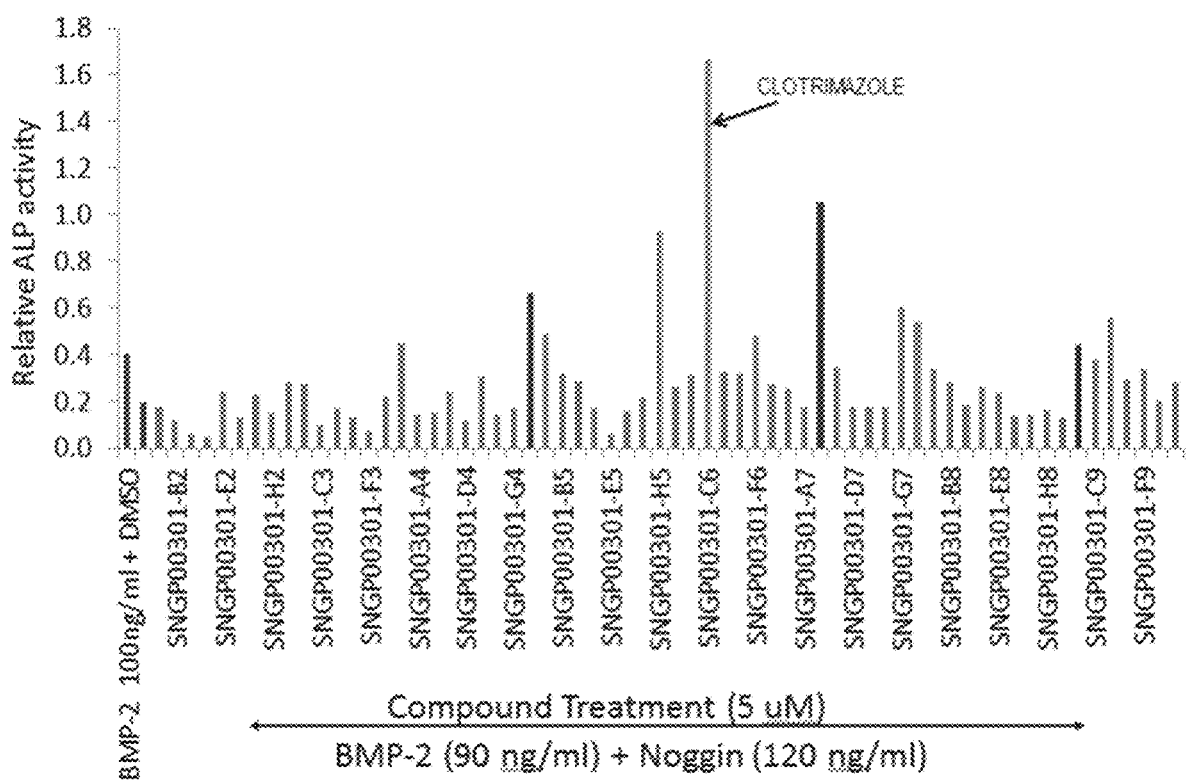
FIG. 4 shows data on the activity of test compounds in a BMP-Noggin competitive ALP assay. Progesterone is SNGP-003-01 H03; capsaicin is SNGP-003-01 H04; salbutamol sulfate is SNGP-003-01 A05; Zardaverine is SNGP-003-01 H05; clotrimazole is SNGP-003-01 C06; Riluzole is SNGP-003-01 F06; (CGS 15943) 9-chloro-2-(furan-2-yl)[1,2,4]triazolo[1,5-c]quinazolin-5-amine is SNGP-003-01 B07; Prazosin is SNGP-003-01 G07; and urapidil hydrochloride is SNGP-003-01 H07. (CGS 15943) 9-chloro-2-(furan-2-yl)[1,2,4]triazolo[1,5-c]quinazolin-5-amine and Capsaicin caused cell lifting from culture plates as determined based on low cell number and low yield of protein after cell harvesting and cell lysis.
Figure 5:
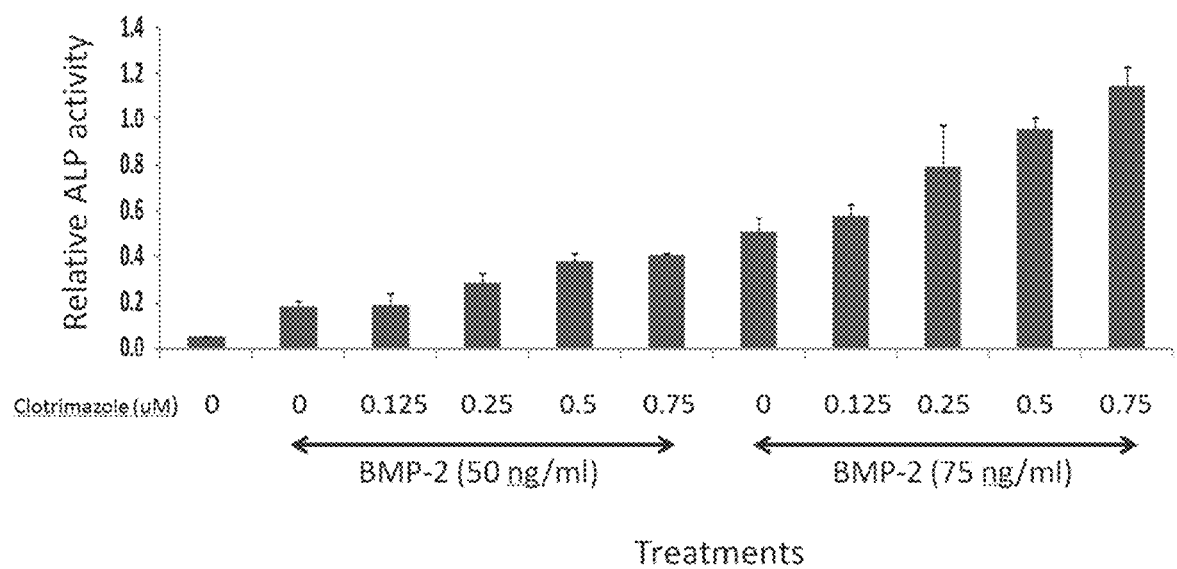
FIG. 5 shows data suggesting dose dependent increase of BMP-induced ALP activity by nanomolar concentrations of clotrimazole.
Figure 6:
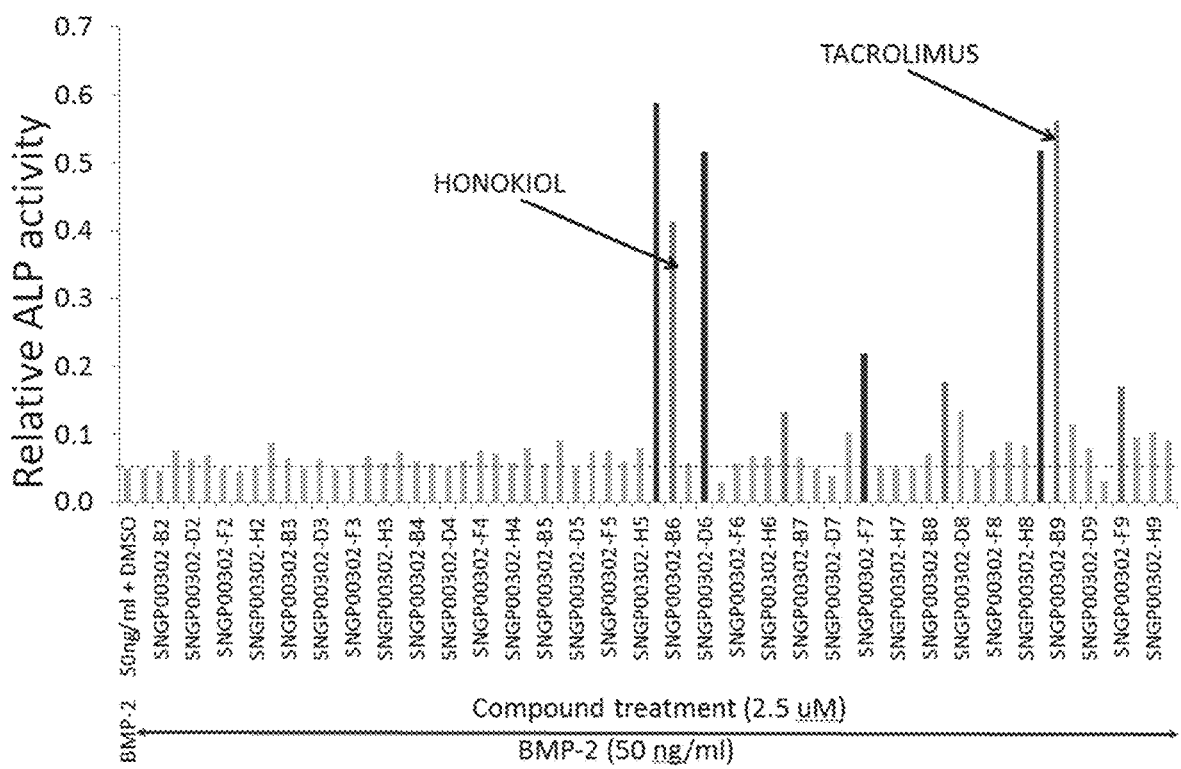
FIG. 6 shows data for the activity of test compounds in the ALP assay. Docetaxel is SNGP-003-02 A06; honokiol is SNGP-003-02 B06; carmofur is SNGP-003-02 D06; Methyltestosterone is SNGP-003-02 A07; itraconazole is SNGP-003-02 F07; triclabendazole is SNGP-003-02 C08; flubendazole is SNGP-003-02 A09; tacrolimus is SNGP-003-02 B09; and trimebutine maleate is SNGP-003-02 F09. Docetaxel, carmofur, itraconazole, and flubendazole caused cell lifting from culture plates.
Figure 7:
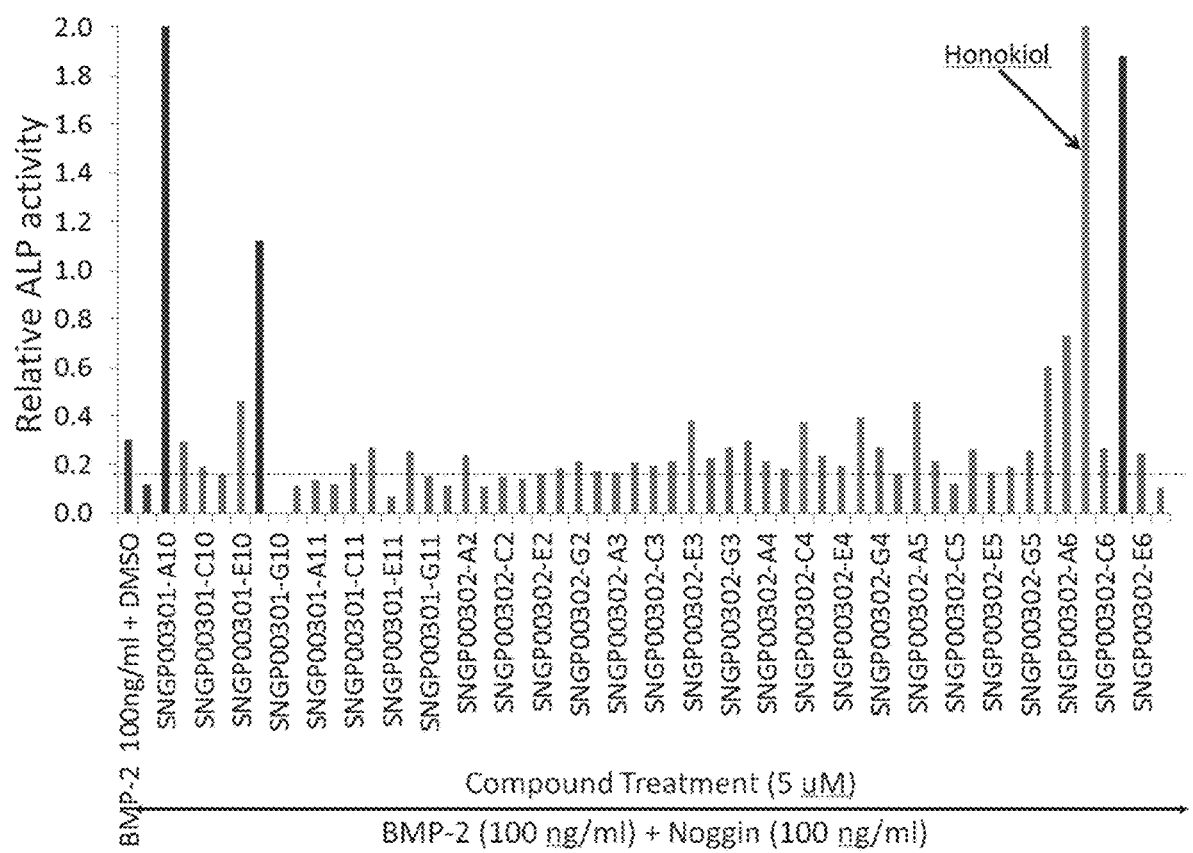
FIG. 7 shows data of activity for test compounds in a BMP-Noggin competitive ALP assay. Ketoconazole is SNGP-003-01 A10; ethynylestradiol is SNGP-003-01 E10; cytarabine is SNGP-003-01 F10; taxifolin is SNGP-003-02 E03; letrozole is SNGP-003-02 C04; ondansetron is SNGP-003-02 F04; alprazolam is SNGP-003-02 A05; perospirone is SNGP-003-02 H05; docetaxel is SNGP-003-02 A06; and honokiol is SNGP-003-02 B06. Ketoconazole and cytarabine caused cell lifting from culture plates.
Figure 8:
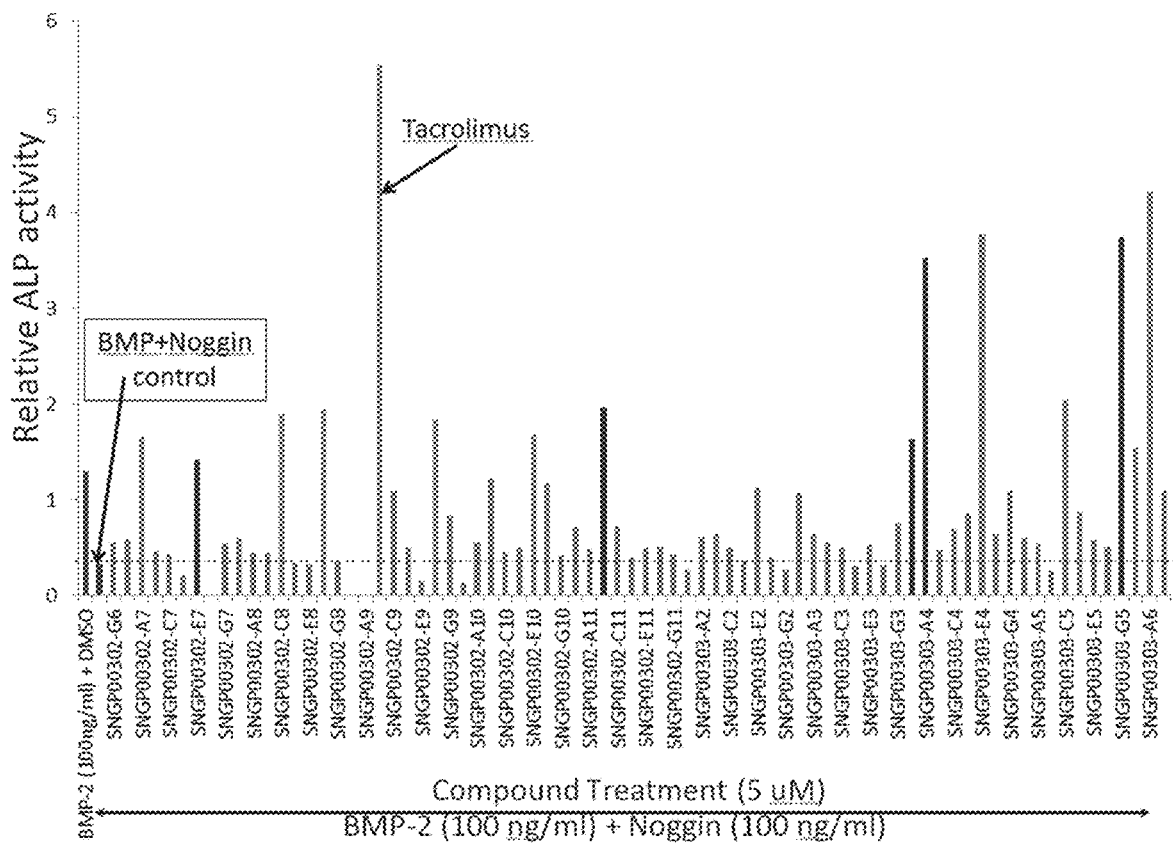
FIG. 8 shows data on the activity of test compounds in a BMP-Noggin competitive ALP Assay. Methyltestosterone is SNGP-003-02 A07; artesunate is SNGP-003-02 E07; triclabendazole is SNGP-003-02 C08; ezetimibe is SNGP-003-02 F08; tacrolimus is SNGP-003-02 B09; trimebutine maleate is SNGP-003-02 F09; megestrol acetate is SNGP-003-02 E10; and oxiconazole nitrate is SNGP-003-02 B11. Artesunate and oxiconazole nitrate caused cell lifting from culture plates.
Figure 9:
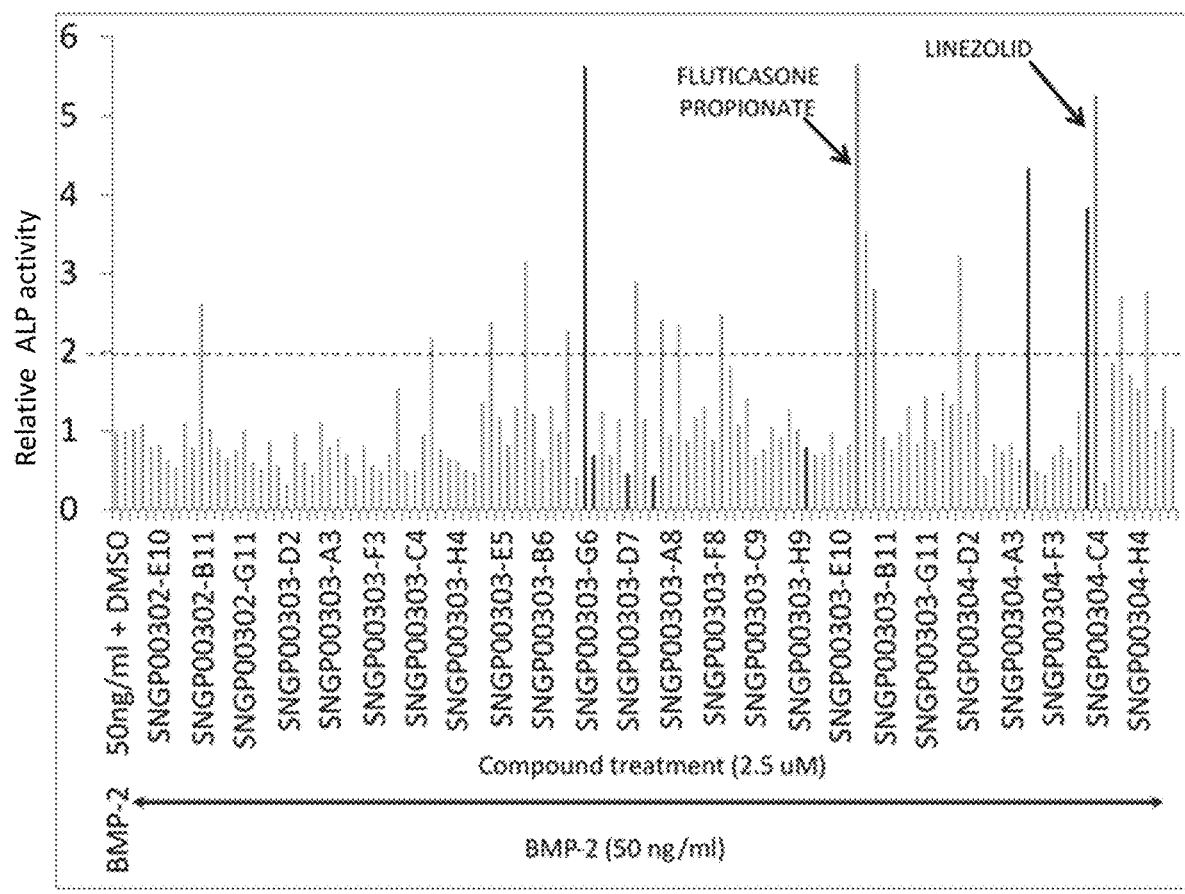
FIG. 9 shows data on the activity of test compounds in an ALP assay. Oxiconazole nitrate is SNGP-003-02 B11; pioglitazone hydrochloride is SNGP-003-03 E04; zolpidem tartarate is SNGP-003-03 D05; fenoldopam mesylate is SNGP-003-03 H05; 2',3'-dideoxyinosine is SNGP-003-03 E06; calcipotriol is SNGP-003-03 G06; icariin is SNGP-003-03 E07; rosiglitazole hydrochloride is SNGP-003-03 H07; oligomycin is SNGP-003-03 B08; rolipram is SNGP-003-03 G08; fluticasone propionate is SNGP-003-03 G10; indinavir sulphate is SNGP-003-03H10; midazolam hydrochloride is SNGP-003-03 A11; bifonazole is SNGP-003-04 C02; calcitriol is SNGP-003-04 C03; vinorelbinee bitatrate is SNGP-003-04 B04; linezolid is SNGP-003-04 C04; irbesartan is SNGP-003-04 F04; and pterostilbene is SNGP-003-04 A05. Calcipotriol, calcitriol, and vinorelbinee bitatrate caused cell lifting from culture plates.
Figure 10:
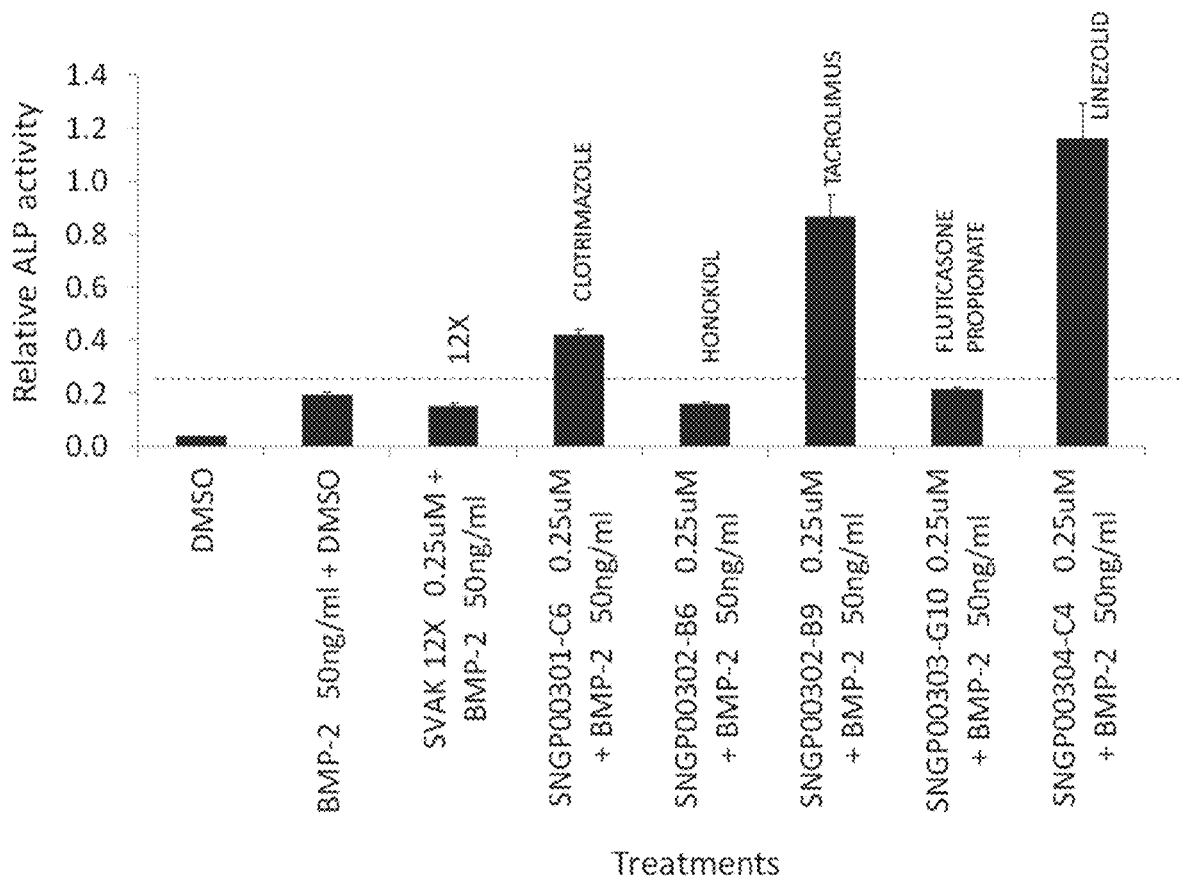
FIG. 10 shows data on the activities in ALP assays for select compounds at 250 nM concentration. SVAK12X is cycloguanil-chemical name 1-(4-chlorophenyl)-2,2-dimethyl-1,3,5-triazine-4,6-diamine.
Figure 11:
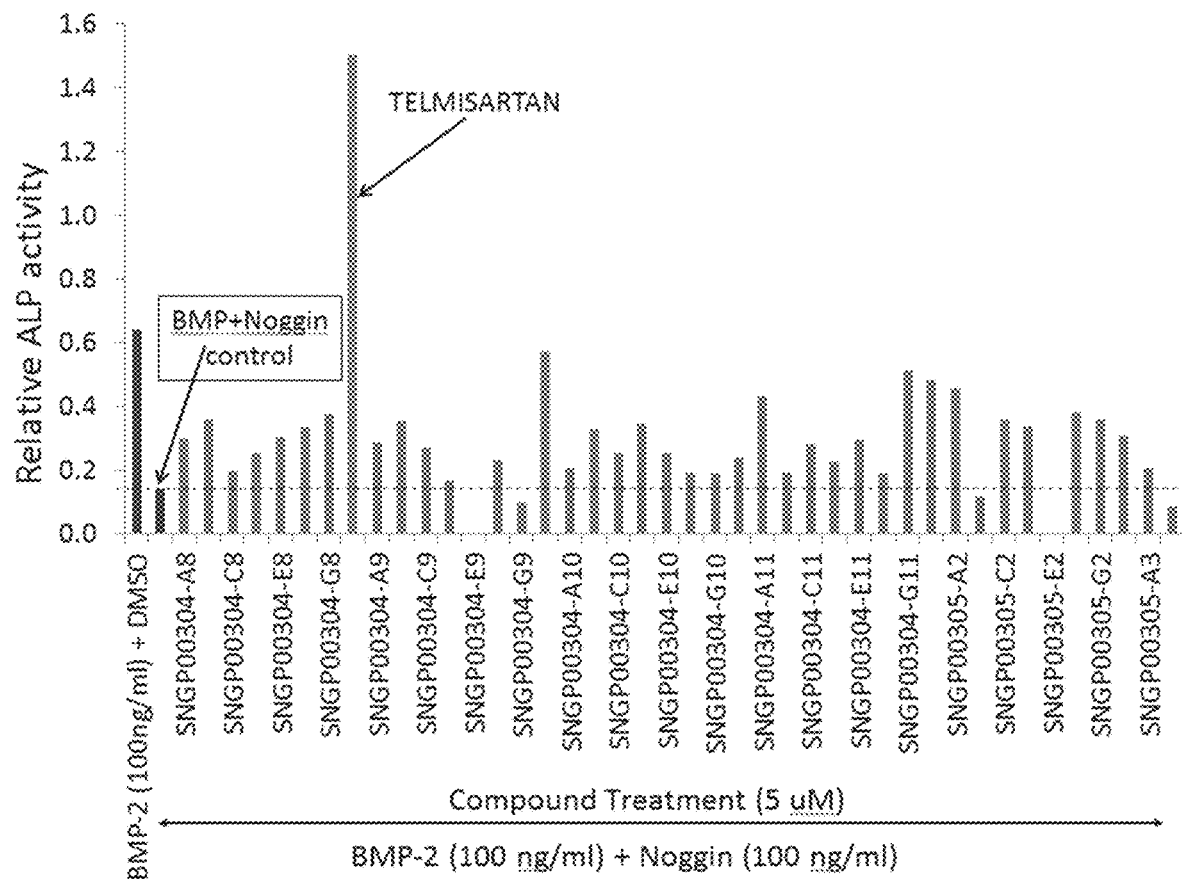
FIG. 11 shows data on the activity of test compounds in a BMP-Noggin competitive ALP assay. Telmisartan is SNGP-003-04H08.
Figure 12:
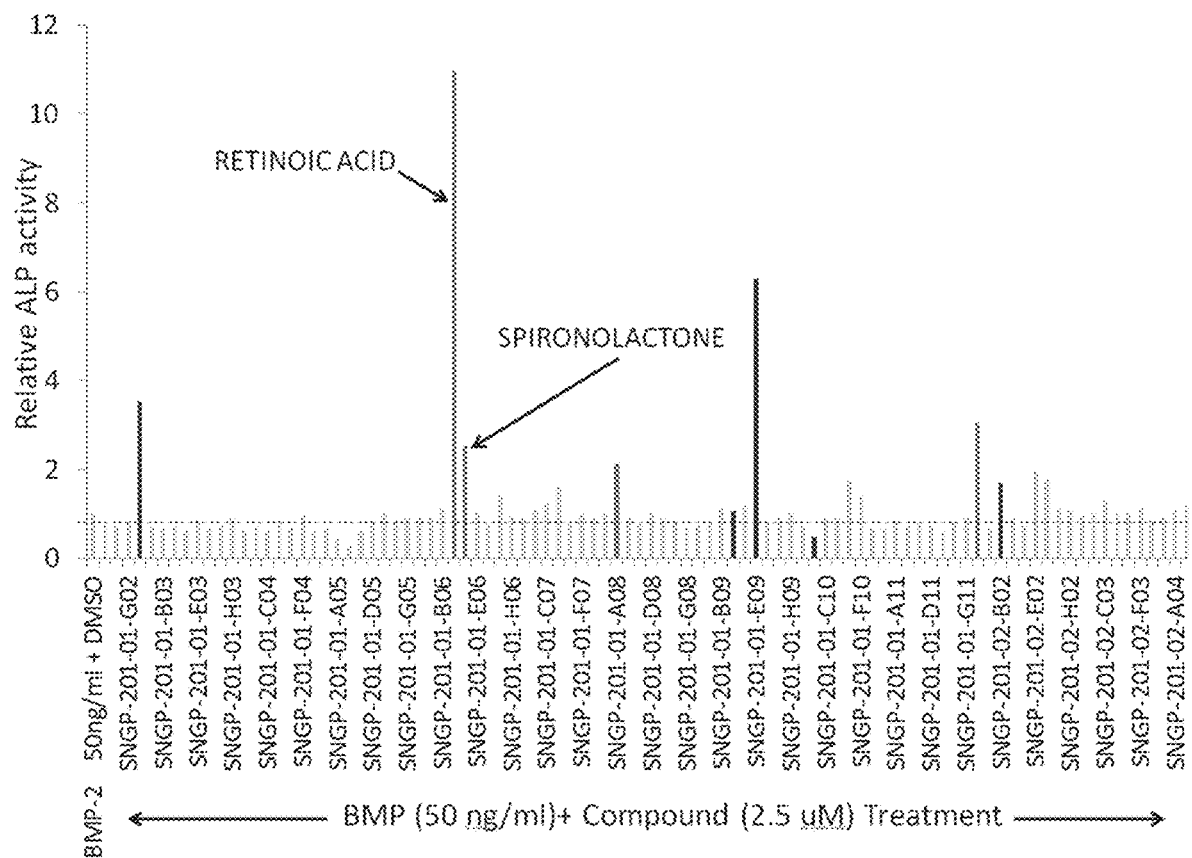
FIG. 12 shows data on the activity of test compounds in an ALP assay. Retinoic acid is SNGP-201-01-006; spironolactone is SNGP-201-01D06; 5-fluorouracil is SNGP-201-01-H02; 3,5,3'-triiodothryonine is SNGP-201-01-A08; econazole nitrate is SNGP-201-01-E09; oxytetracycline hydrochloride is SNGP-201-01-H11. Econazole nitrate and 5-fluorouracil caused cell lifting from culture plates.
Figure 13:
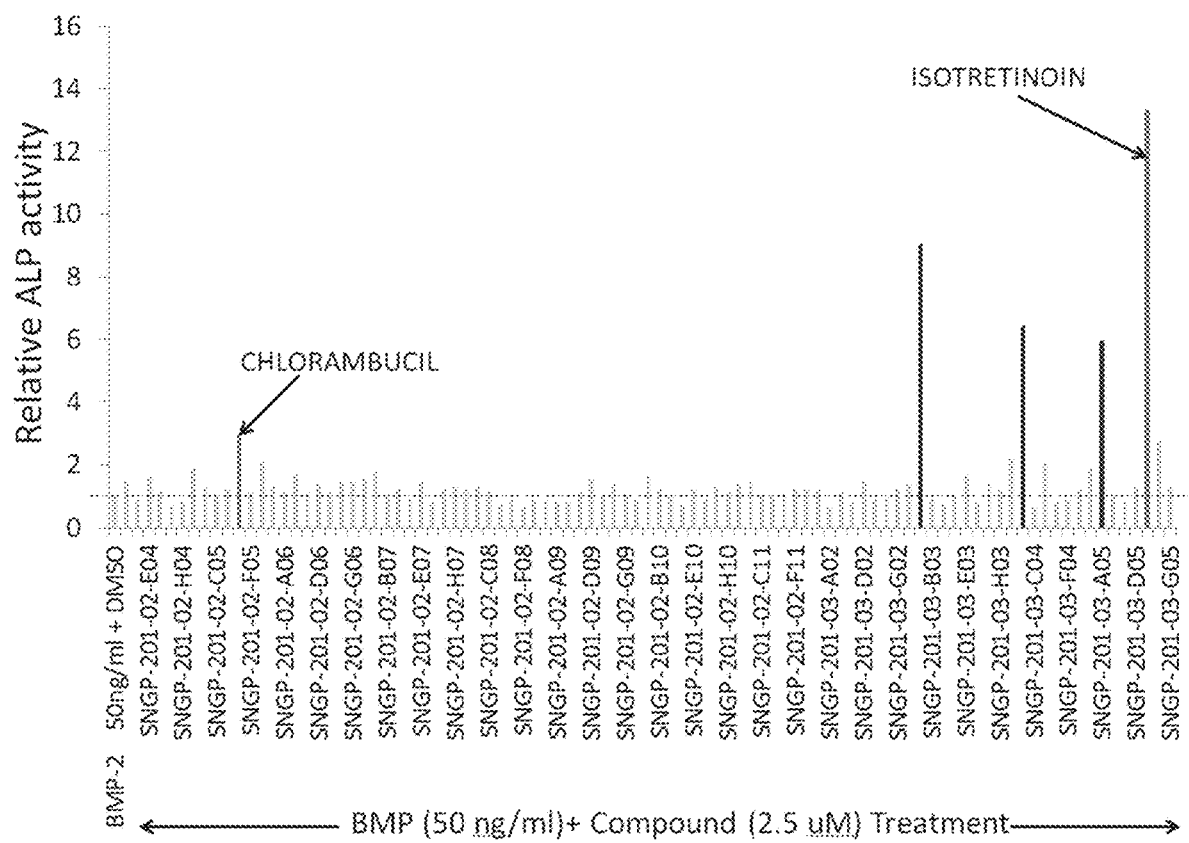
FIG. 13 shows data on the activity of test compounds in an ALP assay. Chlorambucil is SNGP-201-02-E05; isotretinoin is SNGP-201-03-E05; albendazole is SNGP-201-03-A03; mitoxantrone is SNGP-201-03-B04; clomid is SNGP-201-03-A05. Albendazole, mitoxantrone, and clomid caused cell lifting from culture plates.
Figure 14:
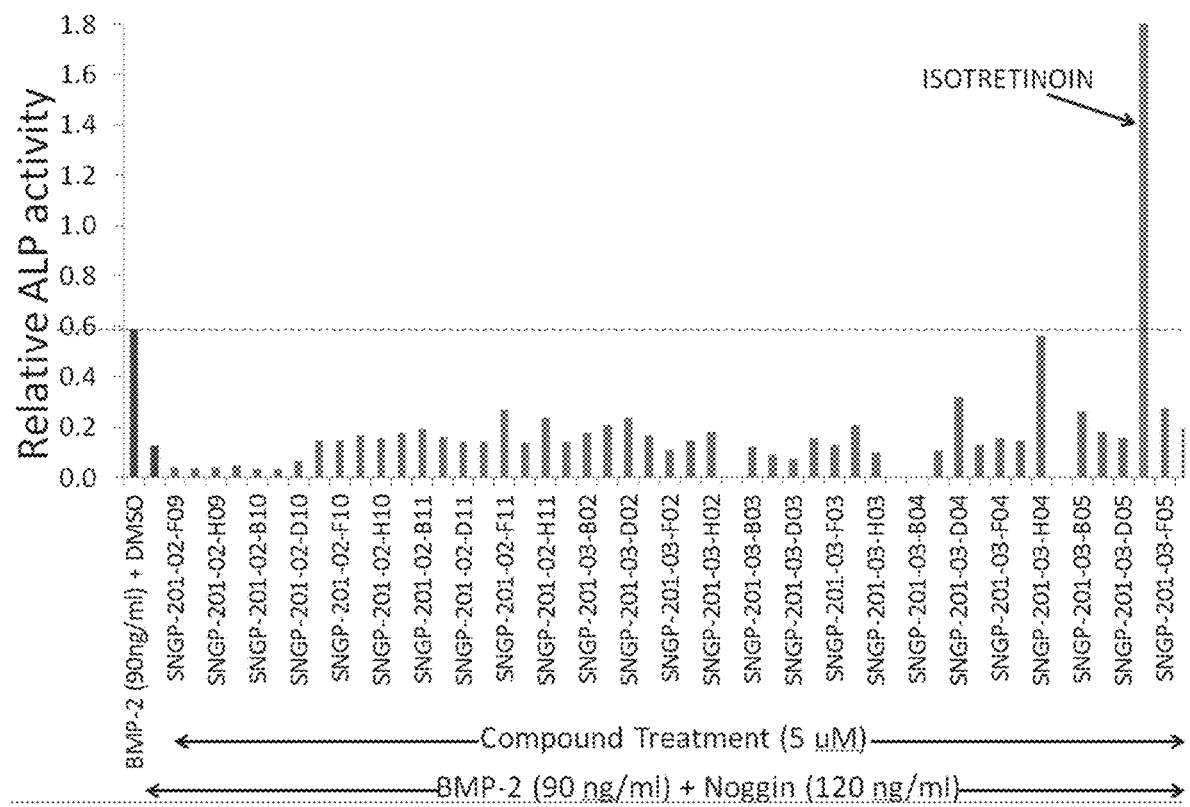
FIG. 14 shows data of activity for test compounds in a BMP-Noggin competitive ALP assay. Isotretinoin is SNGP-201-03-E05.
Figure 15:
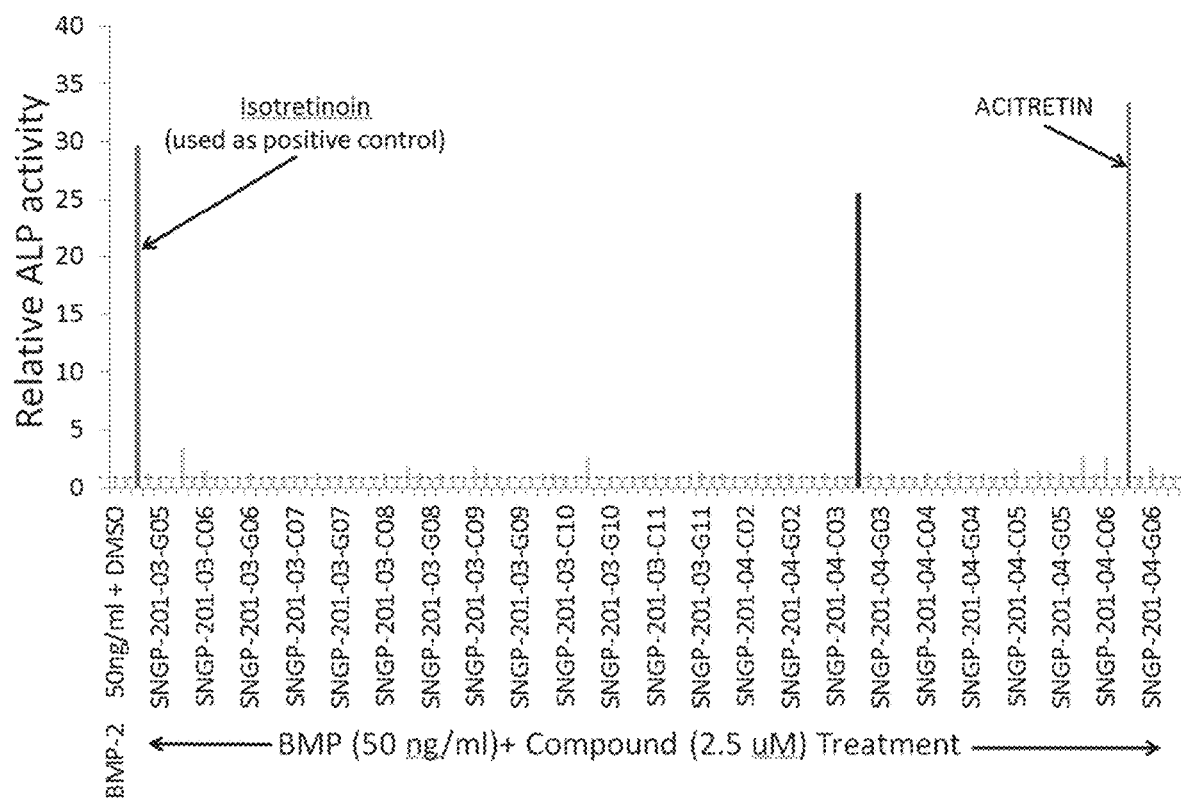
FIG. 15 shows data on the activity of test compounds in an ALP assay. Isotretinoin is SNGP-201-03-E05 and acitretin is SNGP-201-04-E06. Daunorubicin hydrochloride is SNGP-201-04-E03. Daunorubicin hydrochloride caused cell lifting from culture plates.
Figure 16:
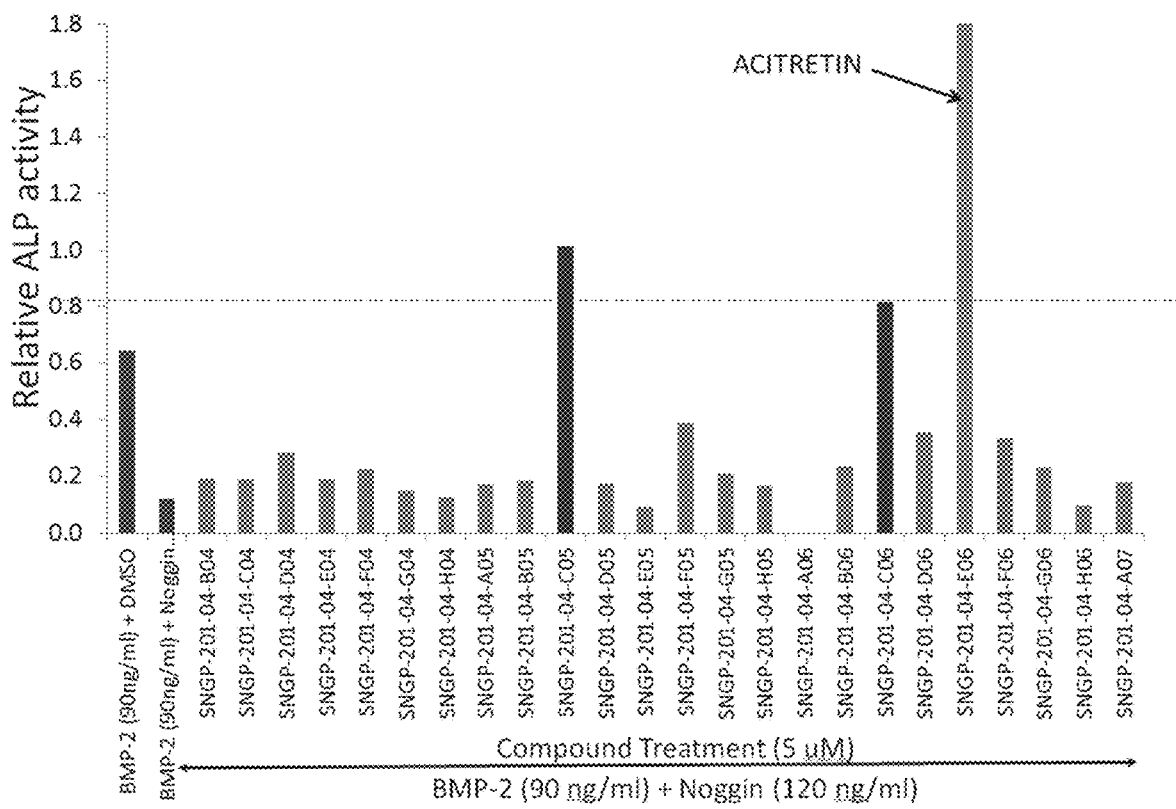
FIG. 16 shows data of activity for test compounds in a BMP-Noggin competitive ALP assay. Acitretin is SNGP-201-04-E06; lovastatin is SNGP-201-04-005; and felodipine is SNGP-201-04-006. Lovastatin and felodipine caused cell lifting from culture plates.
Figure 17:
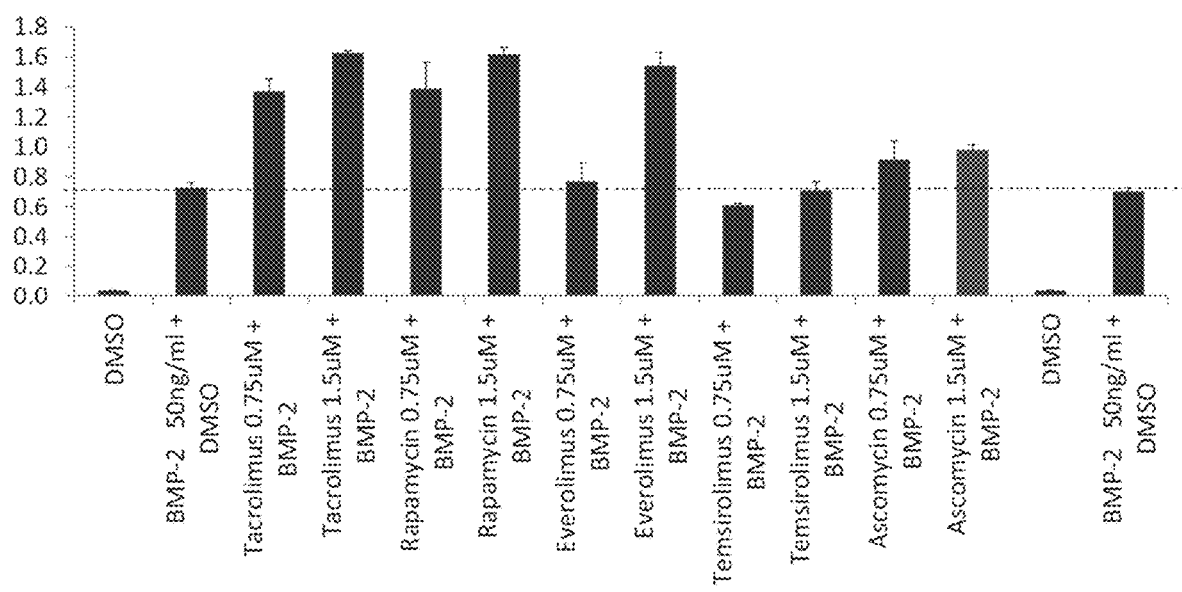
FIG. 17 shows data of activity for macrolide analogs in an ALP activity assay. Vertical axis (Y-axis) is relative ALP activity, and the horizontal axis (X-axis) is treatment.

"Ossification" refers to the process of laying down new bone by cells called osteoblasts. The term includes the growth in healing bone fractures treated by cast or by open reduction and stabilization by metal plate and screws. Ossification can also result in the formation of bone tissue in an extraskeletal location.

The term "bone morphogenetic protein" or "BMP" refers to any one of the family of growth factors or fragments thereof with the ability to induce the formation of bone and/or cartilage. The BMP receptors are typically serine-threonine kinases. It is not intended that BMP refer to any particular protein sequence and may or may not have certain glycosylation patterns attached thereto provided that the molecule has sufficient structural homology to any one of the known BMPs described below and retains some functional ability to promote bone growth, cartilage growth, or osteoblast differentiation. BMPs may be isolated from natural or non-natural sources, such as, but not limited to, recombinant or synthetic methods. References to BMPs generally or a specific BMP, e.g, BMP-2, includes recombinant or synthetically isolated versions unless otherwise provide for herein. Combinations of BMPs are contemplated. BMP-2 is known to induce bone and cartilage formation and play a role in osteoblast differentiation. BMP-3 is known to induce bone formation. BMP-4 is known to regulate the formation of teeth, limbs and bone from mesoderm and play a role in fracture repair. BMP-5 is known to function in cartilage development. BMP-6 is known to play a role in joint integrity and bone formation/repair. BMP-7 and BMP-9 are known to play a role in osteoblast differentiation. BMP-1 is a known metalloprotease that acts on procollagen I, II, and III and is involved in cartilage development.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. The derivative may be a prodrug. Derivatives can be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "calcium phosphate(s)" refers to minerals containing calcium ions together with orthophosphates, metaphosphates or pyrophosphates and optionally hydroxide ions. Tricalcium phosphate is a calcium phosphate with formula $Ca_3(PO_4)_2$. The common mineral apatite has the basic formula $Ca_5(PO_4)_3X$, where X is a ion, typically a halogen or hydroxide ion, or a mixture. Hydroxyapatite refers to apatite where X is mainly hydroxide ion. In certain embodiments, the disclosure contemplates calium phosphates that can further include both silicate ($SiO_4^{4-}$) and carbonate ($CO_3^{2-}$) substituted hydroxyapatites, where the substitution is for one or more of the hydroxy and/or phosphate groups.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

The term "bone graft composition" refers to materials that are substantially physiologically compatible when residing in bone area, void, or exterior site. In certain embodiments, the bone graft composition may be a bone graft matrix such as a collagen sponge or a mixture of polymers and salts.

As used herein, the term "retinoic acid" refers to the all-trans compound (2E,4E,6E,8E)-3,7-dimethyl-9-(2,6,6-trimethylcyclohexen-1-yl)nona-2,4,6,8-tetraenoic acid also known as tretinoin.

Compounds

Compounds derivatives disclosed herein may be used for bone and cartilage growth and related applications. Derivatives of certain compounds are further exemplified below.

In certain embodiments, the disclosure relates to 1-triarylmethyl-1H-imidazole derivatives of formula I:

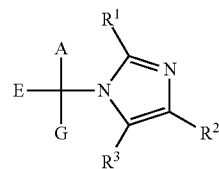

Formula I or a salt thereof, wherein

A, E, and G are each the same or different alkyl, alkynyl, alkenyl, aryl or heteroaryl, wherein A, E, and G are optionally substituted with one or more, the same or different, R$^4$;

R$^1$, R$^2$, and R$^3$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each R$^1$, R$^2$, and R$^3$ are optionally substituted with one or more, the same or different, R$^4$;

R$^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein R$^4$ is optionally substituted with one or more, the same or different, R$^5$; and R$^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is alkynyl.

In certain embodiments, the disclosure relates to 1-triarylmethyl-1H-imidazole derivatives of formula IA:

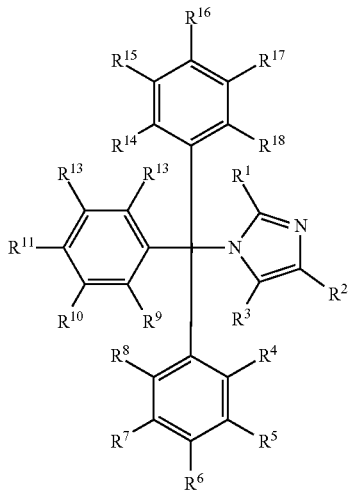

Formula IA or salts thereof wherein, $R^1, R^2, R^3, R^4, R^5, R^6, R^7, R^8, R^9, R^{10}, R^{11}, R^{12}, R^{13}, R^{14}, R^{15}, R^{16}, R^{17}$ and $R^{18}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1, R^2, R^3, R^4, R^5, R^6, R^7, R^8, R^9, R^{10}, R^{11}, R^{12}, R^{13}, R^{14}, R^{15}, R^{16}, R^{17}$ and $R^{18}$ are optionally substituted with one or more, the same or different, $R^{19}$;

$R^{19}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{19}$ is optionally substituted with one or more, the same or different, $R^{20}$; and $R^{20}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1, R^2, R^3, R^4, R^5, R^6, R^7, R^8, R^9, R^{10}, R^{11}, R^{12}, R^{13}, R^{14}, R^{15}, R^{16}$, and $R^{17}$ are hydrogen and $R^{18}$ is a halogen.

In certain embodiments, the disclosure relates to biphenyl-diol derivatives of formula II,

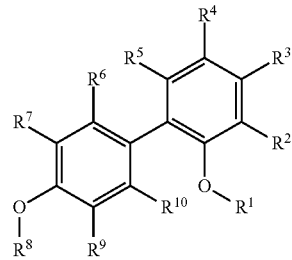

Formula II or salts thereof wherein, $R^1, R^2, R^3, R^4, R^5, R^6, R^7, R^8, R^9$, and $R^{10}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each $R^1, R^2, R^3, R^4, R^5, R^6, R^7, R^8, R^9$, and $R^{10}$, are optionally substituted with one or more, the same or different, $R^{11}$;

$R^{11}$ is alkyl, alkenyl, halogen, nitro, cyano, hydroxy, amino, mercapto, formyl, carboxy, carbamoyl, alkanoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ and $R^9$ are alkenyl.

In certain embodiments, the disclosure relates to macrolide lactone derivatives of formula III,

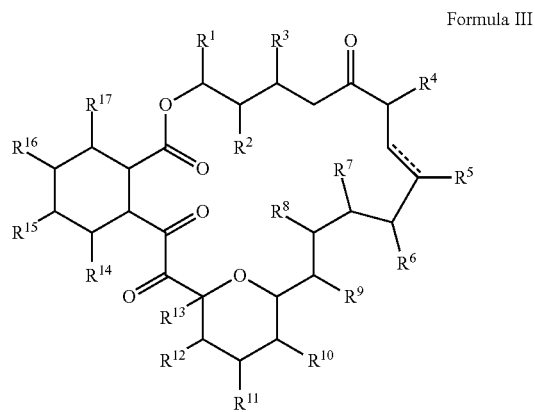

Formula III or salts thereof wherein, the dotted line represents a single or double bond;

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are optionally substituted with one or more, the same or different, $R^{18}$;

$R^{18}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{18}$ is optionally substituted with one or more, the same or different, $R^9$; and $R^{19}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl or alkenyl wherein $R^1$ is substituted with a carbocyclyl substituted with one or more $R^{18}$.

In certain embodiments, $R^2$, $R^3$, $R^4$, $R^5$, $R^7$, $R^9$, $R^{10}$, $R^{12}$, and $R^{13}$ are each the same or different alkyl, alkenyl, hydroxy, or alkoxy.

In certain embodiments, $R^6$, $R^8$, $R^{11}$, $R^{14}$, $R^{15}$, $R^{16}$, and $R^{17}$ are all hydrogen.

In certain embodiments, the disclosure relates to macrolide lactone derivatives of formula IIIA,

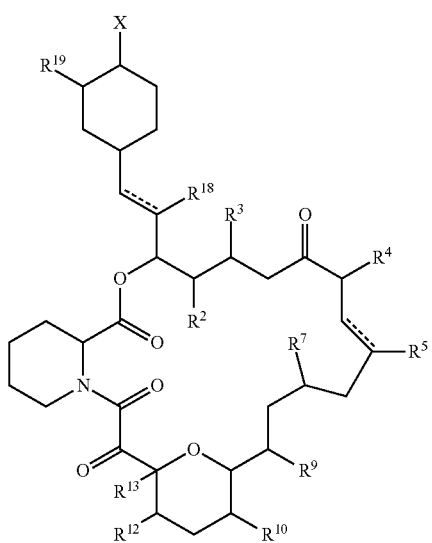

Formula IIIA or salts thereof wherein, the dotted lines each individually represent a single or double bond;

X is hydroxy, amino, mercapto, or halogen;

$R^2$, $R^3$, $R^4$, $R^5$, $R^7$, $R^9$, $R^{10}$, $R^{12}$, $R^{13}$, $R^{18}$, and $R^{19}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, $R^7$, $R^9$, $R^{10}$, $R^{12}$, $R^{13}$, $R^{18}$, and $R^{19}$ are optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$, $R^3$, $R^4$, $R^5$, $R^7$, $R^9$, $R^{10}$, $R^{12}$, $R^{13}$, $R^{18}$, and $R^{19}$ are each the same or different hydrogen, alkyl, alkenyl, halogen, hydroxy, or alkoxy.

In certain embodiments, X is hydroxy or halogen.

In certain embodiments, $R^2$, $R^5$, $R^7$, and $R^{18}$ are alkyl.

In certain embodiments, $R^3$ and $R^{13}$ are hydroxy.

In certain embodiment, $R^4$ is alkenyl.

In certain embodiment, $R^9$, $R^{10}$, and $R^{19}$ are alkoxy.

In certain embodiments, the disclosure relates to steroid derivatives. In certain embodiments, the steroid derivatives have formula IV:

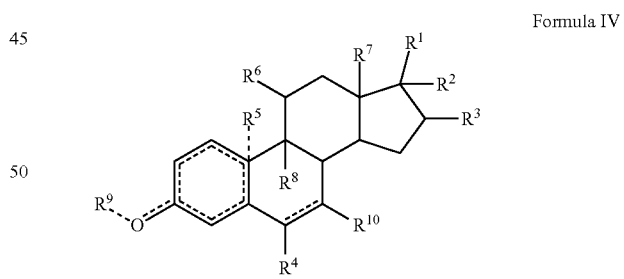

Formula IV or salts thereof wherein, the dotted lines represent an optional bond to provide an absent, single, or double bond a) provided that if the dotted ring is aromatic, then the dotted line between the O and the ring is a single bond and the dotted line between the ring and $R^5$ is absent as $R^5$ is absent and b) provided that if the dotted line between O and the ring is a double bond, then the dotted line between the O and $R^9$ is absent as $R^9$ is absent;

$R^1$, $R^2$, $R^3$, $R^4$, $R^5$, $R^6$, $R^7$, $R^8$, $R^9$, and $R^{10}$ are each the same or different hydrogen, alkyl, alkenyl, alkynyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, and $R^{10}$ are optionally substituted with one or more, the same or different, $R^{11}$;

$R^1$ and $R^2$ may form a carbocyclic or heterocyclic ring optionally substituted with one or more, the same or different, $R^{11}$.

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ and $R^2$ form a 5-membered lactone ring.

In certain embodiments, $R^2$ is hydroxy.

In certain embodiments, $R^{10}$ is hydrogen or mercapto optionally substituted with acetyl.

In certain embodiments, the dotted ring is aromatic and $R^9$ is hydrogen.

In certain embodiments, the disclosure relates to 3-oxo-6,7,8,9,10,11,12,13,14,15,16,17-dodecahydro-3H-cyclopenta[a]phenanthrene-17-carbothioic acid derivatives of formula IVA

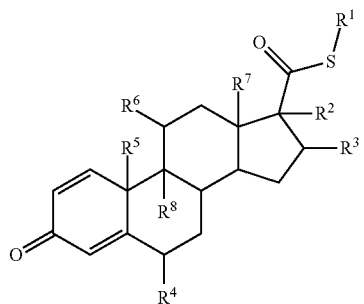

Formula IVA or salts thereof wherein, $R^1$, $R^2$, $R^3$, $R^4$, $R^5$, $R^6$, $R^7$, and $R^8$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, and $R^8$ are optionally substituted with one or more, the same or different, $R^{10}$, $R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is an alkyl substituted with one or more halogens.

In certain embodiments, $R^2$ is hydroxy substituted with an alkanoyl.

In certain embodiments, $R^4$ and $R^8$ are halogen.

In certain embodiments, $R^6$ is hydroxy.

In certain embodiments, the disclosure relates to 3-(4-morpholinophenyl)oxazolidin-2-one derivatives of formula V,

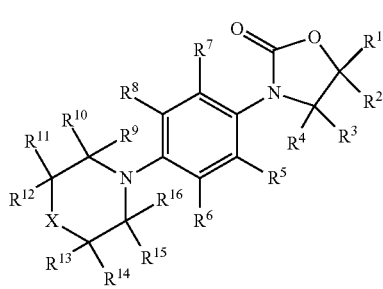

Formula V or salts thereof wherein

X is O, S, or $NR^{17}$ $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are optionally substituted with one or more, the same or different, $R^{18}$;

$R^{18}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{18}$ is optionally substituted with one or more, the same or different, $R^{19}$; and $R^{19}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is O.

In certain embodiments, $R^1$ is alkyl substituted with $R^{18}$.

In certain embodiments, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are all hydrogen.

In certain embodiments, the disclosure relates to 3-(4-morpholinophenyl)oxazolidin-2-one derivatives of formula VI, Formula VI or salts thereof wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ $R^{18}$, $R^{19}$, and $R^{20}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ $R^{18}$, $R^{19}$, and $R^{20}$ are optionally substituted with one or more, the same or different, $R^{21}$;

$R^{21}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{21}$ is optionally substituted with one or more, the same or different, $R^{22}$; and $R^{22}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^2$, and $R^8$ are each the same or different alkyl.

In certain embodiments, $R^{14}$ is carboxy.

In certain embodiments, $R^3$, $R^4$, $R^5$, $R^6$, $R^7$, $R^9$, $R^{10}$, $R^{11}$, $R^{12}$, $R^{13}$, $R^{15}$, $R^{16}$, $R^{17}$ $R^{18}$, $R^{19}$, and $R^{20}$ are hydrogen.

In certain embodiments, the disclosure relates to rentinol derivatives of formula VII,

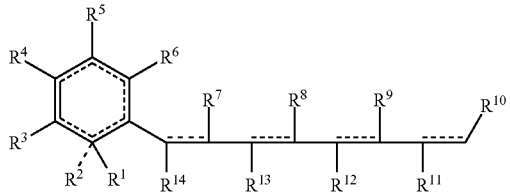

Formula VII or salts thereof wherein the dotted lines represent an optional bond to provide an absent, single, or double bond provided that if the dotted ring is aromatic, then the dotted line between $R^2$ and the ring is absent as $R^2$ is absent;

$R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^2$, $R^6$, $R^{11}$, and $R^{13}$ are alkyl.

In certain embodiments, $R^3$, $R^4$, $R^5$, $R^7$, $R^8$, $R^9$, $R^{12}$, and $R^{14}$ are hydrogen.

In certain embodiments, the dotted ring is aromatic and $R^1$, $R^3$, $R^4$, and $R^6$ are alkyl or alkoxy.

In certain embodiments $R^{10}$ is hydroxy, formyl, or carboxy optionally substituted with $R^{15}$.

In certain embodiments, the disclosure relates to rentinol derivatives of formula VIIA, Formula VIIA or salts thereof wherein
$R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^2$, $R^6$, $R^{11}$, and $R^{13}$ are alkyl.

In certain embodiments, $R^3$, $R^4$, $R^5$, $R^7$, $R^8$, $R^9$, $R^{12}$ and $R^{14}$ are hydrogen.

In certain embodiments, $R^{10}$ is hydroxy, formyl, or carboxy optionally substituted with $R^{15}$.

In certain embodiments, the disclosure relates to rentinol derivatives of formula VIIB,

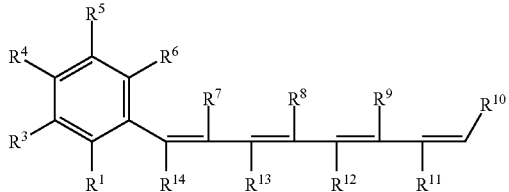

Formula VIIB or salts thereof wherein
$R^1$, $R^3$, $R^4$, $R^5$, $R^6$, $R^7$, $R^8$, $R^9$, $R^{10}$, $R^{11}$, $R^{12}$, $R^{13}$, and $R^{14}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^3$, $R^4$, $R^5$, $R^6$, $R^7$, $R^8$, $R^9$, $R^{10}$, $R^{11}$, $R^{12}$, $R^{13}$, and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^3$, $R^6$, $R^{11}$, and $R^{13}$ are alkyl.

In certain embodiments, $R^4$ is alkoxy.

In certain embodiments, $R^5$, $R^7$, $R^8$, $R^9$, $R^{12}$, and $R^{14}$ are hydrogen.

In certain embodiments, $R^{10}$ is hydroxy, formyl, or carboxy optionally substituted with $R^{15}$.

In certain embodiments, the disclosure relates to 4-(4-(dialkylamino)phenyl)butanoic acid derivatives of formula VIII,

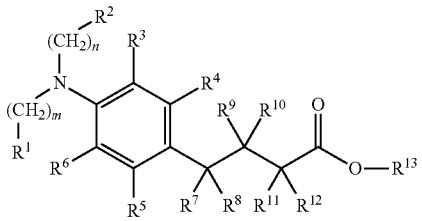

Formula VIII or salts thereof wherein
n is 1, 2, or 3;

m is 1, 2, or 3;

$R^1$ and $R^2$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, aryl sulfonyl, carbocyclyl, aryl, or heterocyclyl, wherein each $R^1$ and $R^2$ are optionally substituted with one or more, the same or different, $R^{14}$;

$R^3$, $R^4$, $R^5$, $R^6$, $R^7$, $R^8$, $R^9$, $R^{10}$, $R^{11}$, $R^{12}$ and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^3$, $R^4$, $R^5$, $R^6$, $R^7$, $R^8$, $R^9$, $R^{10}$, $R^{11}$, $R^{12}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$; and $R^{15}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ and $R^2$ are a halogen.

In certain embodiments, $R^3$, $R^4$, $R^5$, and $R^6$ are hydrogen.

In certain embodiments, $R^7$, $R^8$, $R^9$, $R^{10}$, $R^{11}$, and $R^{12}$ are hydrogen.

In certain embodiments, $R^{13}$ is hydrogen or alkyl.

In certain embodiments, the disclosure relates to macrolide lactone derivatives of formula IX,

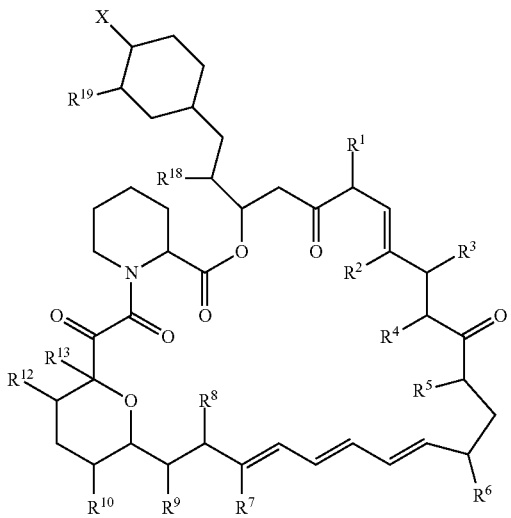

Formula IX or salts thereof wherein,

X is hydroxy, amino, mercapto, halogen, or —O(CH$_2$)$_n$OH wherein X is optionally substituted with one or more, the same or different, $R^{20}$;

n is 2, 3, or 4;

$R^1$, $R^2$, $R^3$, $R^4$, $R^5$, $R^6$, $R^7$, $R^8$, $R^9$, $R^{10}$, $R^{12}$, $R^{13}$, $R^{18}$, and $R^{19}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{12}$, $R^{13}$, $R^{18}$, and $R^{19}$ are optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^2$, $R^3$, $R^4$, $R^5$, $R^6$, $R^7$, $R^8$, $R^9$, $R^{10}$, $R^{12}$, $R^{13}$, $R^{18}$, and $R^{19}$ are each the same or different hydrogen, alkyl, halogen, hydroxy, or alkoxy.

In certain embodiments, X is hydroxy or —O(CH$_2$)$_n$OH.

In certain embodiments, n is 2.

In certain embodiments, $R^1$, $R^2$, $R^5$, $R^6$, $R^7$, $R^{12}$, and $R^{18}$ are alkyl.

In certain embodiments, $R^3$ and $R^{13}$ are hydroxy.

In certain embodiment, $R^4$, $R^8$, and $R^{19}$ are alkoxy.

In certain embodiments, the podophyllotoxin derivative is a compound of formula X,

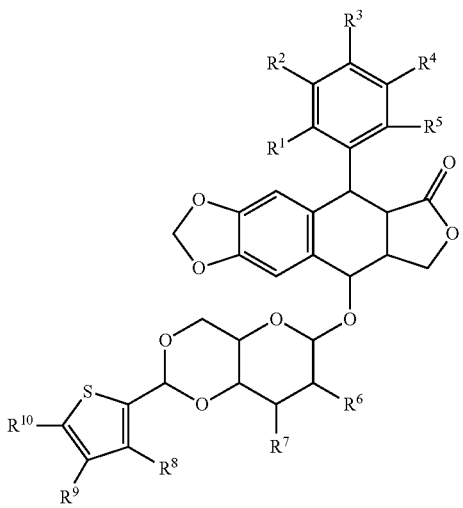

Formula X or salts thereof wherein, $R^1$, $R^2$, $R^3$, $R^4$, $R^5$, $R^6$, $R^7$, $R^8$, $R^9$, and $R^{10}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, and $R^{10}$ are optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^5$, $R^8$, $R^9$, and $R^{10}$ are hydrogen.

In certain embodiments, $R^2$, $R^3$, $R^4$, $R^5$, $R^6$, and $R^7$ are each are each the same or different hydroxy or alkoxy.

In certain embodiments, the aziridine is derivative is a compound of formula XI,

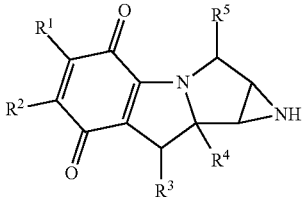

Formula XI or salts thereof wherein, $R^1$, $R^2$, $R^3$, $R^4$, and $R^5$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, and $R^5$ are optionally substituted with one or more, the same or different, $R^6$;

$R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl.
In certain embodiments, $R^2$ is amino.
In certain embodiments, $R^3$ is alkyl substituted with a carbamoyl group.
In certain embodiments, $R^4$ is alkoxy.
In certain embodiments, the nucleoside derivative is a compound of formula XII,

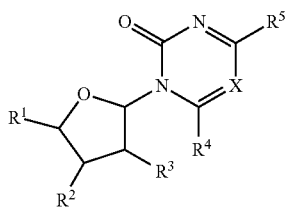

Formula XII or salts thereof wherein,

X is N or $CR^6$;

$R^1$, $R^2$, $R^3$, $R^4$, $R^5$, and $R^6$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^8$; and $R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is hydroxymethyl.
In certain embodiments, $R^2$ is hydroxy.
In certain embodiments, $R^3$ is hydrogen or hydroxy.
In certain embodiments, $R^4$ is hydrogen.
In certain embodiments, $R^5$ is hydrogen or amino.
In certain embodiments, X is CH or N.
In certain embodiments, the vinca alkaloid derivative is a compound of formula XIII,

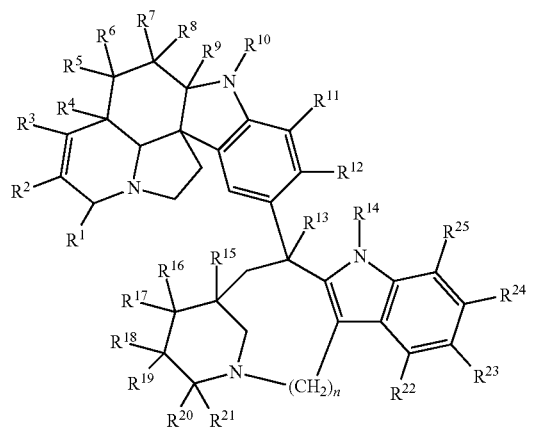

Formula XIII or salts thereof wherein, n is 1 or 2;

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ are optionally substituted with one or more, the same or different, $R^{26}$;

$R^{26}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{26}$ is optionally substituted with one or more, the same or different, $R^{27}$; and $R^{27}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is alkyl.

In certain embodiments, $R^5$ is hydroxy substituted with acetyl.

In certain embodiments, $R^7$ is hydroxy.

In certain embodiments, $R^8$ is carboxy substituted with alkyl.

In certain embodiments, $R^{10}$ is alkyl or formyl.

In certain embodiments, $R^{12}$ is alkoxy.

In certain embodiments, $R^{13}$ is carboxy substituted with alkyl.

In certain embodiments, $R^{16}$ and $R^{18}$ form a double bond.

In certain embodiments, $R^{18}$ is hydroxy.

In certain embodiments, $R^{19}$ is alkyl.

In certain embodiments, $R^1, R^2, R^3, R^6, R^9, R^{11}, R^{14}, R^{15}, R^{16}, R^{17}, R^{20}, R^{21}, R^{22}, R^{23}, R^{24}$, and $R^{25}$ are each hydrogen.

In certain embodiments, the anthracene-9,10-dione derivatives is a compound of formula XIV,

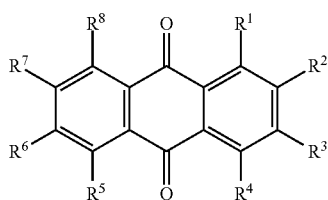

Formula XIV or salts thereof wherein, $R^1$, $R^2$, $R^3$, $R^4$, $R^5$, $R^6$, $R^7$, and $R^8$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, $R^6$, $R^7$, and $R^8$ are optionally substituted with one or more, the same or different, $R^9$;

$R^9$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$; and $R^{10}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the anthracycline derivatives is a compound of formula XV,

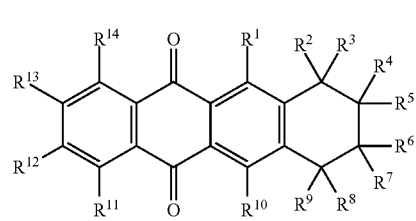

Formula XV or salts thereof wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ and $R^{10}$ are hydroxy.

In certain embodiments, $R^{11}$ is alkoxy.

In certain embodiments, $R^4$ is hydroxy.

In certain embodiments, $R^5$ is alkanoyl.

In certain embodiments, $R^8$ is (oxan-2-yl)oxy or (4-amino-5-hydroxy-6-methyl-oxan-2-yl)oxy.

In certain embodiments, the pazopanib derivatives are compounds of formula XVI,

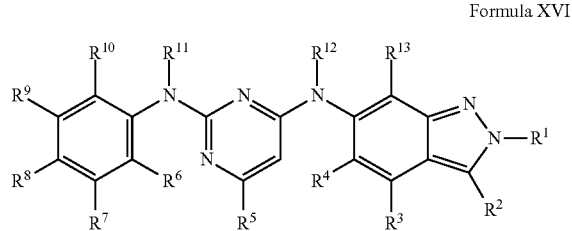

Formula XVI or salts thereof wherein, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$; and $R^{15}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the camptothecin derivative is a compound of the formula XVII,

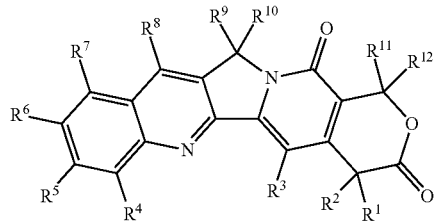

Formula XVII or salts thereof wherein, $R^1$, $R^2$, $R^3$, $R^4$, $R^5$, $R^6$, $R^7$, $R^8$, $R^9$, $R^{10}$, $R^{11}$, and $R^{12}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, and $R^{12}$ are optionally substituted with one or more, the same or different, $R^{13}$;

$R^{13}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{14}$; and $R^{14}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the sunitinib derivatives have formula XVII,

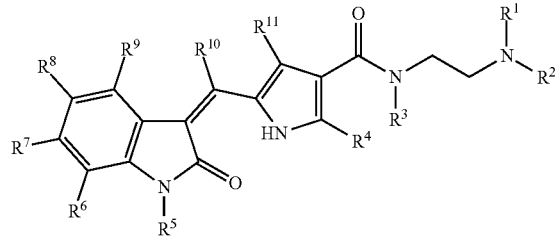

Formula XVIII or salts thereof wherein, $R^1$, $R^2$, $R^3$, $R^4$, $R^5$, $R^6$, $R^7$, $R^8$, $R^9$, $R^{10}$, and $R^{11}$ are each the same or different hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, and $R^{11}$ are optionally substituted with one or more, the same or different, $R^{12}$;

$R^{12}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Evaluations of Compound Activity

BMP-2 and BMP-4 have been established to be important factors in embryonic skeletal development. BMP receptors are transmembrane receptors classified as type I or type II based on sequence homology and contain a Ser/Thr protein kinase domain. BMP ligand binding to type I receptor (BMPR-I) induces the association of BMPR-I and BMPR-II receptors, allowing the constitutively phosphorylated BMPR-II to phosphorylate and activate the latent BMPR-I. After activation of BMPR-I, the receptor regulated (R)-Smad1/5/8 is phosphorylated. Phosphorylation of R-Smad releases it from the receptor complex and forms heterocomplex associating with common Smad (Co-Smad, Smad4). Subsequently, R-Smad/Co-Smad complex translocates into the nucleus and regulates the transcription of target genes by functioning in concert with other proteins as transcription factors. See FIG. 1. BMP activity is regulated prior to receptor recognition by the presence of several structurally distinct extracellular BMP antagonists such as Noggin, follistatin, sclerostatin, chordin, DCR, BMPMER, cerberus, gremlin, DAN, and others.

Structures of the BMPs and its receptors were analyzed to identify the various residues involved in their interaction. Using the LUDI de novo design method a large number of compounds were computationally screened against the binding sites of BMP-receptors to identify lead chemical compounds that mimic BMP-receptor interactions. Small molecules were identified that bind to BMP-receptor binding epitopes or facilitate BMP binding to the receptor or block noggin binding to BMP. Their activity was evaluated by determining the potentiation of alkaline phosphatase activity in sub-optimal doses of BMP in the presence or absence of exogenously added noggin.

Data summary for selected compounds is provided in the table below:

| Compound | Fold increase in BMP-Potentiated ALP activity over BMP control | Fold increase in Noggin-Inhibition ALP Assay over BMP alone control |
| --- | --- | --- |
| Clotrimazole | 7 | 4 |
| Honokiol | 5 | 16 |
| Tacrolimus | 7 | 5 |
| Fluticasone Propionate | 6 | 3 |
| Linezolid | 5 | 3 |
| Telmisartan | 3 | 3 |
| Retinoic acid | 11 | 2 |
| Spironolactone | 3 | 4 |
| Chlorambucil | 3 | 4 |
| Isotretinoin | 30 | 3 |
| Acitretin | 33 | 3 |

The fold-increase in Noggin-inhibition assay is based on BMP-alone control. Further 3 to 5-fold increases were observed when BMP and Noggin control is compared.

Data for additions compounds is provided below.

| Compound | Fold-increase of BMP-induced ALP (over BMP alone control) |
| --- | --- |
| Teniposide | 7.0 |
| Mitomycin C | 12.0 |
| Cytarabine HCl | 2.0 |
| Vinorelbine tartrate | 4.0 |
| Mitoxantrone | 4.0 |
| Plicamycin | 7.0 |
| Vincristine | 5.0 |
| Valrubicin | 3.0 |
| Doxorubicin | 4.0 |
| Pazopanib | 2.5 |
| Topotecan | 4.0 |
| Decitabine | 6.0 |
| Sunitinib | 4.0 |
| Daunomycin, monohydrochloride | 7.0 |
| 9-aminocamptothecin | 10.0 |
| 1-(1,1-diphenylprop-2-yn-1-yl)-1H-imidazole | 7.0 |

In certain embodiments, the disclosure contemplates compositions comprising any of the the compounds herein, or derivatives or substituted forms, such as those in the table, and uses for any of the applications disclosed herein.

Growth Factors

In some embodiments, the disclosure relates to the combined use of growth factor(s) and compounds disclosed herein such as a compound selected from clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salt thereof and one or more growth factors in bone growth applications. Typically, the growth factor is a bone morphogenetic proteins (BMPs), including but not limited to, BMP-1, BMP-2, BMP-2A, BMP-2B, BMP-3, BMP-3b, BMP-4, BMP-5, BMP-6, BMP-7 (OP-1), BMP-8, BMP-8b, BMP-9, BMP-10, BMP-11, BMP-12, BMP-13, BMP-14, BMP-15. BMPs act through specific transmembrane receptors located on cell surface of the target cells.

Non-limiting examples of additional suitable growth factors include osteogenin, insulin-like growth factor (IGF)-1, IGF-II, TGF-beta1, TGF-beta2, TGF-beta3, TGF-beta4, TGF-beta5, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), growth and differentiation factors (GDF)-5 through 9, and osteogenic protein-1 (OP-1). The growth factors may be isolated from synthetic methods, recombinant sources or may be purified from a biological sample. Preferably the growth factors are obtained from a recombinant technology and for clarity certain embodiments include rhBMP-2, rhBMP-4, rhBMP-6, rhBMP-7, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534 hereby incorporated by reference.

In a typical embodiment, a graft composition comprises a matrix, BMP-2, and one or more compound(s) disclosed herein such a compound selected from clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salt thereof in combinations with other growth factors such as GDF-5. In one embodiment, the matrix contains an effective amount of a BMP-2 protein, an rhBMP-2 protein, functional fragments thereof, or combinations thereof. For certain embodiments, the range of concentrations of BMP-2 may be about 1.0 to 4.0 mg/ml and GDF-5 concentrations may be 0.25 to 4.0 mg/ml. Although a graft matrix may be loaded during manufacturing, it is typically loaded just prior to implantation.

The polypeptide of human BMP-2 is 396 amino acids in length, and its gene is localized to chromosome 20p12. BMP-2 belongs to the transforming growth factor-beta (TGF-beta) superfamily. The human amino acid sequence BMP-2 is SEQ ID NO:1 shown below. Amino acids 38-268 are the TGF-beta propeptide domain, and 291-396 are the TGF-beta family N-terminal domain. Amino acids 283-396 are the mature peptide. The mature form of BMP-2 contains four potential N-linked glycosylation sites per polypeptide chain, and four potential disulfide bridges. (SEQ ID NO: 1)

1 MVAGTRCLLA LLLPQVLLGG AAGLVPELGR RKFAAASSGR PSSQPSDEVL SEFELRLLSM 61 FGLKQRPTPS RDAVVPPYML DLYRRHSGQP GSPAPDHRLE RAASRANTVR SFHHEESLEE 121 LPETSGKTTR RFFFNLSSIP TEEFITSAEL QVFREQMQDA LGNNSSFHHR INIYEIIKPA 181 TANSKFPVTR LLDTRLVNQN ASRWESFDVT PAVMRWTAQG HANHGFVVEV AHLEEKQGVS 241 KRHVRISRSL HQDEHSWSQI RPLLVTFGHD GKGHPLHKRE KRQAKHKQRK RLKSSCKRHP 301 LYVDFSDVGW NDWIVAPPGY HAFYCHGECP FPLADHLNST NHAIVQTLVN SVNSKIPKAC 361 CVPTELSAIS MLYLDENEKV VLKNYQDMVV EGCGCR.

In one embodiment, bone morphogenetic protein includes one of the following synthetic peptide fragments of BMP-2: SEQ ID NO: 2 (KIPKASSVPTELSAISTLYLDDD), SEQ ID NO: 3 (CCCCDDDSKIPKASSVPTELSAISTLYL) SEQ ID NO: 4 ($C_{16}H_{31}O$—NH-CCCCGGGSKIPKASSVPTELSAISTLYL) which may be synthesized by FMOC/tBu solid-phase peptide synthesis.

BMP-7 also belongs to the TGF-beta superfamily. It induces cartilage and bone formation. The amino acid sequence of BMP-7 is SEQ ID NO: 5. (SEQ ID NO: 5) 1 MHVRSLRAAA PHSFVALWAP LFLLRSALAD FSLDNEVHSS FIHRRLRSQE RREMQREILS 61 ILGLPHR-PRP HLQGKHNSAP MFMLDLYNAM AVEEGGGPGG QGFSYPYKAV FSTQGPPLAS 121 LQDSHFLTDA DMVMSFVNLV EHDKEFFHPR YHHREFRFDL SKIPEGEAVT AAEFRIYKDY 181 IRERFDNETF RISVYQVLQE HLGRESDLFL LDSRTLWASE EGWLVFDITA TSNHWVVNPR 241 HNLGLQLSVE TLDGQSINPK LAGLIGRHGP QNKQPFMVAF FKATEVHFRS IRSTGSKQRS 301 QNRSKTPKNQ EALRMANVAE NSSSDQRQAC KKHELYVSFR DLGWQDWIIA PEGYAAYYCE 361 GECAFPLNSY MNATNHAIVQ TLVHFINPET VPKPCCAPTQ LNAISVLYFD DSSNVILKKY 421 RNNVVRACGC H. Amino acids 1-29 are a potential signal sequence; 30-431 are the prepropeptide, and 293-431 are the mature protein. The mature form of BMP-7 contains four potential N-linked glycosylation sites per polypeptide chain, and four potential disulfide bridges.

Graft Compositions

In some embodiments, the disclosure relates to a graft composition comprising growth factor(s) and clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof. In some embodiments, these compositions can be created from polymers, bone granules, and ceramics such as calcium phosphates (e.g. hydroxyapatite and tricalcium phosphate), bioglass, and calcium sulphate.

Bioglass refers to materials of $SiO_2$, $Na_2O$, $CaO$, and $P_2O_5$ in specific proportions. The proportions differ from the traditional soda-lime glasses in lower amounts of silica (typically less than 60 mol %), higher amounts of sodium and calcium, and higher calcium/phosphorus ratio. A high ratio of calcium to phosphorus promotes formation of apatite crystals; calcium and silica ions can act as crystallization nuclei. Some formulations bind to soft tissues and bone, some only to bone, some do not form a bond at all and after implantation get encapsulated with non-adhering fibrous tissue, and others are completely absorbed overtime. Mixtures of 35-60 mol % $SiO_2$, 10-50 mol % $CaO$, and 5-40 mol % $Na_2O$ bond to bone and some formulations bond to soft tissues. Mixtures of >50 mol % $SiO_2$, <10 mol % $CaO$, <35 mol % $Na_2O$ typically integrate within a month. Some CaO may be replaced with MgO and some $Na_2O$ may be replaced with $K_2O$. Some CaO can be replaced with $CaF_2$.

In some embodiments, the disclosure relates to a graft composition comprising growth factor(s) and compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof and/or polysaccharides such as hyaluronate, cellulose or cellulose derivatives such as, but not limited to, hydroxypropyl cellulose, methyl cellulose, ethyl cellulose, and carboxymethyl cellulose. Typically, cellulose derivatives are used in graft compositions that produce a paste or putty.

In some embodiments, the disclosure relates to a bone graft composition comprising a bone morphogenetic protein and clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salt thereof and a graft matrix. The matrix is typically a polymer designed to hold bone compatible salts, such as calcium phosphates, for replacement during bone growth. An example is a bovine Type I collagen embedded with biphasic calcium phosphate granules. Optionally, matrix compositions may also include one or more agents that support the formation, development and growth of new bone, and/or the remodeling thereof. Typical examples of compounds that function in, such a supportive manner include extracellular matrix-associated bone proteins such as alkaline phosphatase, osteocalcin, bone sialoprotein (BSP) and osteocalcin, phosphoprotein (SPP)-1, type I collagen, fibronectin, osteonectin, thrombospondin, matrix-gla-protein, SPARC, and osteopontin.

In certain embodiments, the graft matrix can be made up of a hydrogel polymer. Typically, a hydrogel is made-up of acrylate polymers and copolymers substituted with an abundance of hydrophilic groups, such as terminal hydroxy or carboxyl groups. In certain embodiments, the graft composition is biodegradable. In certain embodiments, the matrix comprises homopolymers and copolymers consisting of gylcolide and lactide. For certain embodiments, the graft composition comprises a matrix of hydroxyethylmethacrylate or hydroxymethylmethyacrylate polymers containing hydroxyapatite in a mineral content approximately that of human bone. Such a composition may also be made with crosslinkers comprising an ester, anhydride, orthoester, amide, or peptide bond. In some embodiments, crosslinkers contain the following polymers: polyethylene glycol (PEG), polylactic acid, polyglycolide or combinations thereof.

In certain embodiments, the graft can be any material that is porous including those that have macroporosity (mean pore diameter greater than or equal to 100 µm), mesoporosity (mean pore diameter less than 100 µm but greater than or equal to 10 µm) and microporosity (mean pore diameter less than 10 µm). The pores may be of any size, shape or distribution, or within a predetermined tolerance. In addition, the pores can be interconnecting or non-interconnecting. In certain embodiments, the graft composition can be a plurality of porous or non-porous granules. The specific surface area of the graft can vary. For example, when the graft is a porous granule, the specific surface area can range from about 0.1 m$^2$/g to about 100 m$^2$/g.

Suitable polymers useful for preparing the graft include, but are not limited to, homopolymers or copolymers of monomers selected from L-lactide; L-lactic acid; D-lactide; D-lactic acid; glycolide; alpha-hydroxybutyric acid; alpha-hydroxyvaleric acid; alpha-hydroxyacetic acid; alpha-hydroxycaproic acid; alpha-hydroxyheptanoic acid; alpha-hydroxydecanoic acid; alpha-hydroxymyristic acid; alpha-hydroxyoctanoic acid; alpha-hydroxystearic acid; hydroxybutyrate; hydroxyvalerate; beta-propiolactide; beta-propiolactic acid; gamma-caprolactone; beta-caprolactone; epsilon-caprolactone; gamma-butyrolactone; pivalolactone; tetramethylglycolide; tetramethylglycolic acid; dimethylglycolic acid; trimethylene carbonate; dioxanone; those monomers that form liquid crystal polymers; those monomers that form cellulose; those monomers that form cellulose acetate; those monomers that form carboxymethylcellulose; those monomers that form hydroxypropylmethylcellulose; polyurethane precursors including macrodiols selected from polycaprolactone, poly(ethylene oxide), poly(ethylene glycol), poly(ethylene adipate), poly(butylene oxide), and a mixture thereof, isocyanate-functional compounds selected from hexamethylene diisocyanate, isophorone diisocyanate, cyclohexane diisocyanate, hydrogenated methylene diphenylene diisocyanate, and a mixture thereof, and chain extenders selected from ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof, and any combination of two or more of the foregoing.

In certain embodiments, the graft composition may contain one or more antibiotics and/or anti-inflammatory agents. Suitable antibiotics include, without limitation, nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

In certain embodiments, compounds disclosed herein can be combined with the graft preoperatively as well as intra-operatively. Where the compound is combined pre-operatively, it can be combined with the graft as part of a manufacturing process where the compound could be applied to the scaffold in a buffered solution and then subsequently lyophilized or air dried. The compound may also be applied by spray drying or other coating methods. The graft could then be subsequently packaged and sterilized. Where the compound is combined intra-operatively with the graft, the graft can be dipped or coated with a buffered solution including the compound and then applied to the bone site to be repaired.

In certain embodiments, the graft can further include an osteogenic material to provide a viable cell population to the bone repair site. The osteogenic material can be obtained from both autogenic sources as well as allogenic sources, such as cadaveric sources or tissue banks Suitable osteogenic material can include, for example, viable cell sources such as stem cells, multipotent cells, pluripotent cells, osteoprogenitor cells, pre-osteoblasts, mature osteoblasts, and blends and mixtures thereof.

In certain embodiments, the osteogenic material is obtained from autogenic and/or allogenic human bone marrow, and according to another embodiment, the osteogenic material is obtained from autogenic and/or allogenic human lipoaspirate. Both the bone marrow and lipoaspirate can be processed to further enhance the desired cell population for example by filtration, separation and/or concentration. In order to preserve the viability of the cell population of the osteogenic material, the osteogenic material is typically combined with the graft matrix and osteoinductive material at or near the time of the implantation procedure.

Methods

Bone grafting is possible because bone tissue, unlike most other tissues, has the ability to regenerate if provided the space into which to grow with appropriate chemical signals. With regard to synthetic grafts, as native bone grows, it typically replaces most or all of the artificial graft material, resulting in an integrated region of new bone. However, with regard to certain embodiments of the disclosure, it is not intended that new bone must remove all artificial material. In addition, with regard to certain embodiments of the disclosure, it is not intended that graft location need contact any other bone of the skeletal system.

In certain embodiments, the disclosure relates to a method of forming bone comprising implanting a graft composition comprising a compound disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof, in a subject. In certain embodiments, the disclosure relates to methods of forming bone comprising implanting a graft composition comprising a bone morphogenetic protein and compound(s) disclosed herein, such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof, in a subject. The graft may be the result of a void created by surgical removal or created as a result of an attempt to correct a physical abnormality of a bone, such as but not limited to, cranial bones; frontal, parietal, temporal, occipital, sphenoid, ethmoid; facial bones; mandible, maxilla, palatine, zygomatic, nasal, lacrimal, vomer, inferior nasal conchae; shoulder girdle; scapula or shoulder blade, clavicle or collarbone; in the thorax; sternum, manubrium, gladiolus, and xiphoid process, ribs; in the vertebral column; cervical vertebrae, thoracic vertebrae; lumbar vertebrae; in the arms, humerus, radius, ulna; in the pelvis; coccyx; sacrum, hip bone (innominate bone or coxal bone); in the legs; femur, patella, tibia, and fibula. It is contemplated that the graft may be added for cosmetic purposes, e.g., cheek augmentation. In the case of a broken bone or removal of a bone during surgery, it may be desirable to secure movement of bone structure with a fixation system and remove the system after bone forms in the implanted graft.

With regard to prostheses, it may be desirable to grow bone between existing bone and an implanted device, or in preparation of an implanted device, such as in the case of a hip replacement, knee replacement, and dental implant, i.e., artificial tooth root used to support restorations that resemble a tooth or group of teeth.

In some embodiments, the disclosure relates to three-dimensional structures made of biocompatible and biodegradable bone graft materials in the shape of the bone infused with compositions disclosed herein to promote bone growth. Implants can be used to support a number of prostheses. A typical implant consists of a titanium device. In certain embodiments, the graft compositions disclosed herein contain implants.

With regard to a sinus augmentation or alveolar ridge augmentation, surgery may be performed as an outpatient under general anesthesia, oral conscious sedation, nitrous oxide sedation, intravenous sedation or under local anesthesia. Bone grafting is used in cases where there is a lack of adequate maxillary or mandibular bone in terms of depth or thickness. Sufficient bone is needed in three dimensions to securely integrate with the root-like implant. Improved bone height is important to assure ample anchorage of the root-like shape of the implant.

In a typical procedure, the clinician creates a large flap of the gingiva or gum to fully expose the bone at the graft site, performs one or several types of block and onlay grafts in and on existing bone, then installs a membrane designed to repel unwanted infection-causing bacteria. Then the mucosa is carefully sutured over the site. Together with a course of systemic antibiotics and topical antibacterial mouth rinses, the graft site is allowed to heal. The bone graft produces live vascular bone and is therefore suitable as a foundation for the dental implants.

In certain embodiments, the disclosure relates to methods of performing spinal fusion using compositions disclosed herein. Typically this procedure is used to eliminate the pain caused by abnormal motion of the vertebrae by immobilizing the vertebrae themselves. Spinal fusion is often done in the lumbar region of the spine, but the term is not intended to be limited to method of fusing lumbar vertebrae. Patients desiring spinal fusion may have neurological deficits or severe pain which has not responded to conservative treatment. Conditions where spinal fusion may be considered include, but are not limited to, degenerative disc disease, spinal disc herniation, discogenic pain, spinal tumor, vertebral fracture, scoliosis, kyphosis (i.e, Scheuermann's disease), spondylolisthesis, or spondylosis.

In certain embodiments, different methods of lumbar spinal fusion may be used in conjunction with each other. In one method, one places the bone graft between the transverse processes in the back of the spine. These vertebrae are fixed in place with screws and/or wire through the pedicles of each vertebra attaching to a metal rod on each side of the vertebrae. In another method, one places the bone graft between the vertebra in the area usually occupied by the intervertebral disc. In preparation for the spinal fusion, the disc is removed entirely. A device may be placed between the vertebrae to maintain spine alignment and disc height.

The intervertebral device may be made from either plastic or titanium or other suitable material. The fusion then occurs between the endplates of the vertebrae. Using both types of fusion are contemplated.

In certain embodiments, the disclosure relates to methods of growing bone at a desired area by locally administering a pharmaceutical formulation containing a compound disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof, to the area of desired bone growth with or without the presence of a graft composition or bone growth matrix optionally in combination with a growth factor such as a bone morphogenetic protein. In certain embodiments, the disclosure contemplates administering the pharmaceutical compositions between vertebra, e.g., in the area usually occupied by in the intervertebral disc, to form a spinal fusion.

Cartilage Repair

Cartilage is typically composed of chondroblasts, Type I and Type II collagen fibers, elastin fibers, and proteoglycans. Typical locations within the human body to find cartilage are the joints between bones, the ear, the nose, the elbow, the knee, the ankle, and the intervertebral discs. Cartilage can become damaged because of trauma or disease. In some embodiments, the disclosure relates to using compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof for the repair or regeneration of cartilage such as articular cartilage repair or regeneration or intervertebral disc cartilage repair or regeneration.

Articular cartilage repair is typically done to restore the cartilage on the surface of a bone, i.e., hyaline cartilage. Osteochondrial autografts or allografts may be performed. In certain embodiments, the disclosure contemplates methods of cartilage repair comprising transplanting sections of cartilage and/or bone to a location where cartilage and/or bone was removed and placing a compound disclosed herein such as herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof about the surrounding area, e.g., by injections at the site of transplantation. Bone with its cartilage covering may be removed from the same or a different joint and replanted into the hole left from removing degraded bone and cartilage. The transplanted bone and cartilage are typically taken from areas of low stress.

In autologous chondrocyte implantation, cartilage cells are typically extracted arthroscopically from normal articular cartilage of the subject that is located in a nonload-bearing area, e.g., the intercondylar notch or the superior ridge of the femoral condyles, and the cells are replicated, in vitro, in the presence of growth factors. In certain embodiments, the disclosure relates to replicating cartilage cells comprising mixing hyaline cartilage and a compound disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof, under conditions such that the cartilage cells replicate. Typically this is done by adding other growth factors to the cartilage replicating medium, e.g., cartilage-derived morphogenetic proteins and/or BMP proteins. The replicated chondrocytes are implanted to the desired area, e.g., injected about the site of the area for repair optionally in combination with either a membrane or a matrix comprising growth factors such as a CDMP, BMP protein or a compound disclosed herein.

Repair of articular cartilage may be performed by marrow stimulating procedures sometimes referred to as microfracture surgery. Damaged cartilage is typically ablated by, e.g., drilling or pounding, exposing the underlying bone sometimes referred to as a microfracture. The subchondal bone typically generates a blood clot followed by cartilage regeneration. In some embodiments the disclosure relates to methods of generating cartilage by disrupting bone underlying articular cartilage and placing a compound disclosed herein about the area of disruption, e.g., by injecting compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof about the site of disrupted bone for the improved repair or regeneration of cartilage optionally in combination with a growth factor such as a CDMP and/or BMP protein. Alternatively it is contemplated that the compounds are administered to the subject in a pharmaceutical composition before, during or after the procedure. In another alternative, it is contemplated that a collagen matrix is implanted at the site of the exposed underlying bone to improve chondrogenic differentiation of mesenchymal stem cells. It is also contemplated that the subject may optionally be postoperative injected with compounds disclosed herein, hyaluronic acid, and/or mesenchymal stem cells, e.g., obtained from autologous peripheral blood progenitor cells.

Inflammation of the synovial membrane in a joint causes swelling and joint surface destruction. Removing excess fluid and material by a lavage or debridement frequently resolves arthritic knee inflammation and pain. In certain embodiments, the disclosure relates to the use of compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof before, during, or after a lavage or debridement inside a joint, e.g., arthroscopic lavage, arthroscopic debridement. In arthroscopic debridement, joint material or degenerative cartilage it typically removed by injecting a fluid and removing it with a vacuum.

An intervertebral disc (IVD) is found in between two vertebrae. The IVD contains different tissue types such as the annulus fibrosus (AF), the nucleus pulposus (NP), and end-plates. The AF is made up of mainly collagen type I. The amount of collagen type I decreases and collagen type II increase gradually nearer the NP which is mostly collagen type II dispersed within a proteoglycan-rich gelatinous matrix surrounding the NP.

Porous silk scaffolds may be used for a variety of tissue-engineering applications, such as the regeneration of bone and cartilage. Removal of sericin from silk reduces immunogenic responses. Silk may form a desired sponge-like structure by freeze-drying a silk solution. Bone marrow mesenchymal stem cells (BMSC) may be incorporated into porous silk scaffolds wrapped around a silicone NP substitute to form an artificial intervertebral disc. In certain embodiments, it is contemplated that compounds disclosed herein may be used to generate a matrix of annulus fibrosus by mixing with mesenchymal stem cells and growth factors. In certain embodiments, the disclosure contemplates implanting a fabricated intervertebral disc into a subject wherein the disc comprises annulus fibrosus tissue and placing a compound disclosed herein about the site of the implant location, e.g., by injection, optionally in combination with a growth factor such as a cartilage-derived morphogenetic protein (CDMP), e.g., CDMP-1 or CDMP-2, and/or bone morphogenetic proteins, e.g., BMP-7 or BMP-14. The fabricated disc may comprise a NP area with a hydrogel polymer/copolymer matrix or a collagen and/or hyaluronan and/or chondroitin-6-sulfate copolymer. A variety of stem cells, such as mesenchymal stem cells, synovium-derived stem cells (SDSCs), or notochord cells, may be used for rejuvenation of NP cells.

Therapeutic Applications

In some embodiments, the disclosure relates to pharmaceutical compositions comprising compounds disclosed herein for therapeutic applications. In some embodiments, the disclosure relates to methods of treating bone degenerative disorders, such as osteoporosis, osteitis deformans ("Paget's disease of bone"), bone metastasis (with or without hypercalcaemia), multiple myeloma, primary hyperparathyroidism, or osteogenesis imperfecta. Osteoporosis is a disease of bones that leads to an increased risk of fracture. In osteoporosis, the bone mineral density (BMD) is reduced, bone microarchitecture is disrupted, and the amount and variety of proteins in bone is altered. Osteoporosis is most common in women after menopause, when it is called postmenopausal osteoporosis, but may also develop in men, and may occur in anyone in the presence of particular hormonal disorders and other chronic diseases or as a result of medications, specifically glucocorticoids, when the disease is called steroid- or glucocorticoid-induced osteoporosis (SIOP or GIOP).

Osteoporotic fractures are those that occur in situations where healthy people would not normally break a bone; they are therefore regarded as fragility fractures. Typical fragility fractures occur in the vertebral column, rib, hip and wrist. The diagnosis of osteoporosis can be made using conventional radiography by measuring the bone mineral density (BMD).

In some embodiments, the disclosure relates to treating bone degenerative disorders by administering pharmaceutical composition described herein in combination with other agents, such as calcium carbonate and calcium citrate, vitamin D, cholecalciferol, 1,25-dihydroxycholecalciferol, calcitriol, estrogen, testosterone, raloxifene, pamidronate, neridronate, olpadronate, alendronate (Fosamax), ibandronate (Boniva), risedronate (Actonel), zoledronate (Zometa, Aclasta), etidronate (Didronel), clodronate (Bonefos, Loron), or tiludronate (Skelid).

In some embodiments, the disclosure relates to using compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof in the treatment of chondrodystrophies. Typically an effective amount of a pharmaceutical composition comprising the compound is administered to a subject diagnosed with, at risk of, or exhibiting symptoms of osteoarthritis, achondroplasia, costochondrits, relapsing polychondritis, or articular cartilage damage. The pharmaceutical compositions may provide pain relief or slow down the progression of damage delaying joint replacement (knee replacement) surgery.

In some embodiments, the disclosure relates to using compounds disclosed herein such as clotrimazole, honokiol, magnolol, tacrolimus, pimecrolimus, sirolimus, everolimus, temsirolimus, spironolactone, fluticasone, fluticasone propionate, fluticasone furoate, linezolid, telmisartan, chlorambucil, retinol, isotretinoin, acitretin, etretinate, retinoic acid (tretinoin), teniposide, mitomycin C, cytarabine, decitabine, vinblastine, vincristine, vindesine, vinorelbine, valrubicin, doxorubicin, daunorubicin, epirubicin, idarubicin, mitoxantrone, pixantrone, plicamycin, pazopanib, topotecan, camptothecin, irinotecan, sunitinib, derivatives, or salts thereof in the treatment of a degenerative intervertebral disc. Typically an effective amount of a pharmaceutical composition comprising the compound is administered to a subject diagnosed with, at risk of, or exhibiting symptoms of a degenerative disc. The compositions may be administered orally or injected directly into an intervertebral disc (IVD), e.g., into the annulus fibrosus (AF) and/or the nucleus pulposus (NP) optionally in combination with a growth factor such as a cartilage-derived morphogenetic protein (CDMP), e.g., CDMP-1 or CDMP-2, or a bone morphogenetic protein, e.g., BMP-7 or BMP-14.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds of the disclosure contain a hydrogen-donating heteroatom (e.g. NH), the disclosure also covers salts and/or isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxy group is bonded to any group that, when administered to a mammalian subject, cleaves to form a free hydroxy group. Examples of prodrugs include, but are not limited to, acetate, formate, and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethyl cellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein or compound delivery systems. Proteins and/or compounds can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXPERIMENTAL

Compound Screenings

Compounds were selected by virtual screening for development based on computational modeling, docking, and in silico screening. The structural data revealed that the surfaces of BMPs have binding epitopes for BMPR-IA interaction involving the main chain amide groups of amino acids L51 and D53 with minor contribution from the hydrophobic interactions. Two hydrogen bonds are formed between L51 (main chain amide and carbonyl) of BMP-2 and Q86 of BMPR-IA. The core structure of BMPR-II shares the same pattern of disulfide connectivity as ActR-II, with disulfide bonds. In an earlier analysis a hypothetical complex between BMPR-II and BMP2, created by superimposing BMPR-II in the position of ActR-II in the ternary complex between ActR-II, BMP2, and BMPR-IA, suggested that BMPR-II makes similar overall ligand binding contacts to BMP2 as does ActR-II. From Residues Tyr67, Trp85, and Phe115 of BMPRII are in the main hydrophobic patch and Lys81, Ser86, Glu93, and Tyr113 are also important binding determinants. In addition, His87 and Tyr40 confer specificity in BMPR-II ligand binding. Mutational analysis has identified A34, H39, S88, L90, and L100 residues as binding determinants of BMP-2 for BMPR-II and ActR-II. See Sebald et al., Biol Chem, 2004, 385(8):697-710.

Crystal structure of BMPR-II was superimposed on to the ActR-IIB of ternary complex consisting of BMP-2 dimer/BMPR-IAEC/ActR-IIB using a web based tool Superpose. Using these superposed structures a new hypothetical ternary complex consisting of BMP-2/BMPR-IAEC/BMPR-II was modelled. The surface area (A2) for each residue was calculated and the percent solvent accessible contact area (%

SA) of the model ternary complex of BMP-2/BMPR-IAEC/BMPR-II and individual monomer structures, and the position (Pos) and name of the amino acid residues in the binding interface of both the receptors, BMPR-IA and BMPR-II that bind to BMP-2 were identified.

LUDI de novo design method of Accelrys Discovery Studios 3.0 and also NCC library of compounds, which contains Phase I, II, and III drugs, were used against the receptor regions that bind to BMP. The BMP binding region of receptors is divided into ten sub regions (with some overlapping residues) for LUDI runs. The binding site defined as spheres of radius 10 angstrom covering the amino acids in the regions. The LUDI de novo design method against these ten regions derived 300 novel small molecules that were chemically synthesized for cell-based screening assays. LUDI against the BMPR-IA and BMPR-II regions that bind to BMP-2 were also used to obtain molecules from NCC library that are drug molecules from Phase I, II or III.

The BMP-potentiating activities of compounds may be evaluated by monitoring several markers of the osteoblastic phenotype corresponding to various time points during phenotype differentiation of C2C12 cells towards terminally differentiated osteoblasts.

Cell Culture

Mouse C2C12 cells and Dulbecco's modified Eagle's medium (DMEM) were purchased from ATCC (Manassas, Va.). The non-heat inactivated fetal bovine serum (FBS) was purchased from HyClone Laboratories, Inc. (Logan, Utah). The C2C12 cells at passages 5 to 10 were subcultured in T-75 $cm^2$ flasks in DMEM supplemented with 10% FBS at 37° C. in 5% $CO_2$ with humidification. When the flasks reached 80% confluence, the cells were trypsinized and seeded in triplicate.

Alkaline Phosphatase (ALP) Assay

The C2C12 cells were plated at 200,000 cells/well in 6-well plates and grown overnight in DMEM containing 10% FBS. On day 2, the culture medium was replaced with DMEM containing 2% FBS and the cells were treated with various concentrations of compound for 24 hours. On day 3, the culture medium was replaced with DMEM containing 2% FBS and the cells were treated with 50 ng/ml of BMP-2 and various concentrations of compound for 72 hours. The cells were washed with phosphate-buffered saline (PBS) and lysed by addition of lysis buffer (10 mM Tris-HCl pH 8.0, 1 mM $MgCl_2$ and 1.0% Triton X-100). The cell lysates were centrifuged for 5 minutes at 13,000×g. The supernatant was removed and the aliquots were assayed for ALP activity and protein amount. The ALP activity was measured in triplicate using an ALP assay kit (Sigma-Aldrich, St. Louis, Mo.) in microtiter plates. The protein amount was determined with Bio-Rad protein assay reagent (Bio-Rad, Hercules, Calif.) using bovine serum albumin (BSA) as a standard. The ALP activity (nmoles of p-nitrophenol per ml) was normalized to the protein amount (nmoles of p-nitrophenol per μg).

BMP-Noggin Competitive Alkaline Phosphatase (ALP) Assay

The C2C12 cells were plated at 200,000 cells/well in 6-well plates and grown overnight in DMEM containing 10% FBS. On day 2, the culture medium was replaced with DMEM containing 2% FBS and the cells were treated with 90-100 ng/ml of BMP-2 (as noted in each experiment), various concentrations of compound, and 100-120 ng/ml of noggin (as noted in each experiment) for 72 hours. The cells were washed with phosphate-buffered saline (PBS) and lysed by addition of lysis buffer (10 mM Tris-HCl pH 8.0, 1 mM $MgCl_2$ and 1.0% Triton X-100). The cell lysates were centrifuged for 5 minutes at 13,000×g. The supernatant was removed and the aliquots were assayed for ALP activity and protein amount. The ALP activity was measured in triplicate using an ALP assay kit (Sigma-Aldrich, St. Louis, Mo.) in microtiter plates. The protein amount was determined with Bio-Rad protein assay reagent (Bio-Rad, Hercules, Calif.) using bovine serum albumin (BSA) as a standard. The ALP activity (nmoles of p-nitrophenol per ml) was normalized to the protein amount (nmoles of p-nitrophenol per μg).

Collagen Disc Implantation with Macrolides in Rat Ectopic Model

Sprague Dawley rats about 5-6 weeks of age were chest implanted with a collagen disc (diameter of 1.0 cm and height of 2.0 mm; total volume of 150 cubic millimeters) and doses of macrolides in the absence of BMP-2. After 4 weeks the rats were sacrificed and evaluated for bone growth. See table below. De novo bone formation is demonstrated locally with sirolimus, everolimus, and tacrolimus. In certain embodiments, the disclosure contemplates local bone formation for fracture repair, segmental bone defects, spine fusion, bone grafting, and regional bone enhancement for osteopenic bones before they fracture (e.g. hip, vertebral body, etc) by deliver locally to induce local bone formation.

| Drug | Dose (mM) | Volume | Carrier | Animal # with Xray: 1...2...3...4 | Results | Ave. |
|---|---|---|---|---|---|---|
| Sirolimus | 0 | 100 ul | collagen | 0, 0, 0, 0 | No bone (0 of 4) | 0 |
| | 10 | 100 ul | collagen | 0, (1), 0, 0 | Bone (1 of 4) | 0.25 |
| | 15 | 100 ul | collagen | 0, 0, 0, (2) | Bone (1 of 4) | 0.5 |
| | 20 | 100 ul | collagen | 0, 0, (3), 0 | Bone (1 of 4) | 0.75 |
| | 0 | 100 ul | collagen | 0, (1), 0, 0 | Bone (1 of 4) | 0.25 |
| | 25 | 100 ul | collagen | (1), 5, 0, 5 | Bone (3 of 4) | 2.75 |
| | 30 | 100 ul | collagen | x, 4, 5, 5 | Bone (3 of 4) | 3.5 |
| | 35 | 100 ul | collagen | 3, 5, 4, 5 | Bone (4 of 4) | 4.25 |
| Everolimus | 0 | 100 ul | collagen | 0, 0, 0, 0 | No bone (0 of 4) | 0 |
| | 10 | 100 ul | collagen | 0, 0, 0, 0 | No bone (0 of 4) | 0 |
| | 15 | 100 ul | collagen | 5, 0, (2), 3 | Bone (3 of 4) | 2.5 |
| | 20 | 100 ul | collagen | 4, 3, 4, 4 | Bone (4 of 4) | 3.75 |
| | 0 | 100 ul | collagen | 0, 0, 0, 0 | No bone (0 of 4) | 0 |
| | 25 | 100 ul | collagen | 5, 5, 5, 4 | Bone (4 of 4) | 4.75 |
| | 30 | 100 ul | collagen | 5, 5, x, 5 | Bone (3 of 4) | 3.75 |
| | 35 | 100 ul | collagen | 4, 5, 5, 5 | Bone (4 of 4) | 4.75 |

-continued

| Drug | Dose (mM) | Volume | Carrier | Animal # with Xray: 1...2...3...4 | Results | Ave. |
|---|---|---|---|---|---|---|
| Tacrolimus | 0 | 100 ul | collagen | 0, 0, 0, 0 | No bone (0 of 4) | 0 |
| | 10 | 100 ul | collagen | 0, 0, 0, 0 | No bone (0 of 4) | 0 |
| | 25 | 100 ul | collagen | 4, 5, 4, 4 | Bone (4 of 4) | 4.25 |
| | 35 | 100 ul | collagen | 2, 5, 4, 5 | Bone (4 of 4) | 4 |
| | 0 | 100 ul | collagen | 0, 0, 0, 0 | No bone (0 of 4) | 0 |
| | 15 | 100 ul | collagen | 0, 2, 0, 0 | Bone (1 of 4) | 0.5 |
| | 20 | 100 ul | collagen | 0, 5, 6, 2 | Bone (3 of 4) | 3.25 |
| | 30 | 100 ul | collagen | 0, 3, 5, 2 | Bone (3 of 4) | 2.5 |

The invention claimed is:

1. A method of forming bone in vivo comprising implanting a graft composition comprising calcium phosphates and tacrolimus in a subject such that bone forms in the graft, wherein the graft composition does not contain a growth factor.

2. The method of claim 1, wherein more than 0.7 mg of tacrolimus is present per 150 mm$^3$ of bone graft volume.

3. The method of claim 1, wherein said calcium phosphates are hydroxyapatite and tricalcium phosphate.

4. A method of performing spinal fusion comprising implanting a bone graft composition comprising collagen or hydrogel matrix and tacrolimus in a subject such that bone forms in the graft between two vertebrae of a subject, wherein the graft composition does not contain a growth factor.

5. The method of claim 4, wherein the subject has symptoms of back pain.

6. The method of claim 4, wherein the subject is diagnosed with a degenerative disc.

7. The method of claim 4, wherein more than 0.7 mg of tacrolimus is present per 150 mm$^3$ of bone graft volume.

8. The method of claim 4, wherein the bone graft composition comprises a further comprises calcium phosphates.

9. The method of claim 8, wherein said calcium phosphates are hydroxyapatite and tricalcium phosphate.

10. A method of performing spinal fusion comprising implanting a bone graft composition comprising calcium phosphates and tacrolimus in a subject such that bone forms in the graft between two vertebrae of a subject, wherein the graft composition does not contain a growth factor.

11. The method of claim 10, wherein the subject has symptoms of back pain.

12. The method of claim 10, wherein the subject is diagnosed with a degenerative disc.

13. The method of claim 10, wherein more than 0.7 mg of tacrolimus is present per 150 mm$^3$ of bone graft volume.

14. The method of claim 10, wherein said calcium phosphates are hydroxyapatite and tricalcium phosphate.

* * * * *

SEQUENCE LISTING

<160> NUMBER OF SEQ ID NOS: 5

<210> SEQ ID NO 1
<211> LENGTH: 396
<212> TYPE: PRT
<213> ORGANISM: Homo sapiens

<400> SEQUENCE: 1

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270
```

```
Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
        290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 2
<211> LENGTH: 23
<212> TYPE: PRT
<213> ORGANISM: Homo sapiens

<400> SEQUENCE: 2

Lys Ile Pro Lys Ala Ser Ser Val Pro Thr Glu Leu Ser Ala Ile Ser
1               5                   10                  15

Thr Leu Tyr Leu Asp Asp Asp
            20

<210> SEQ ID NO 3
<211> LENGTH: 28
<212> TYPE: PRT
<213> ORGANISM: Homo sapiens

<400> SEQUENCE: 3

Cys Cys Cys Cys Asp Asp Asp Ser Lys Ile Pro Lys Ala Ser Ser Val
1               5                   10                  15

Pro Thr Glu Leu Ser Ala Ile Ser Thr Leu Tyr Leu
            20                  25

<210> SEQ ID NO 4
<211> LENGTH: 29
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Where N is ACETYLATED
<220> FEATURE:
<221> NAME/KEY: MOD_RES
<222> LOCATION: (1)..(1)
<223> OTHER INFORMATION: Where N is the  N terminal
<220> FEATURE:
<221> NAME/KEY: MOD_RES
<222> LOCATION: (1)..(1)
<223> OTHER INFORMATION: Where N  = C16H31O-NH

<400> SEQUENCE: 4

Asn Cys Cys Cys Cys Gly Gly Gly Ser Lys Ile Pro Lys Ala Ser Ser
1               5                   10                  15

Val Pro Thr Glu Leu Ser Ala Ile Ser Thr Leu Tyr Leu
            20                  25
```

<210> SEQ ID NO 5
<211> LENGTH: 431
<212> TYPE: PRT
<213> ORGANISM: Homo sapiens

<400> SEQUENCE: 5

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

-continued

```
Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Asn Val Val Arg Ala Cys Gly Cys His
                420                 425                 430
```